United States Patent
Perrino

(10) Patent No.: US 6,632,665 B1
(45) Date of Patent: Oct. 14, 2003

(54) HUMAN GENE ENCODING 3'-5' EXONUCLEASE

(75) Inventor: Fred W. Perrino, Winston-Salem, NC (US)

(73) Assignee: Wake Forest University, Winston-Salem, NC (US)

(*) Notice: Subject to any disclaimer, the term of this patent is extended or adjusted under 35 U.S.C. 154(b) by 79 days.

(21) Appl. No.: 09/634,137

(22) Filed: Aug. 8, 2000

Related U.S. Application Data

(60) Provisional application No. 60/147,985, filed on Aug. 9, 1999, and provisional application No. 60/148,018, filed on Aug. 10, 1999.

(51) Int. Cl.$^7$ ............... C12N 15/55; C12N 15/85; C12N 15/79
(52) U.S. Cl. ............ 435/325; 435/252.3; 435/199; 536/23.2
(58) Field of Search ................ 435/199, 252.3, 435/325; 536/23.2, 23.5

(56) References Cited

FOREIGN PATENT DOCUMENTS

| WO | WO 91/09955 | 7/1991 |
|---|---|---|
| WO | WO 92/20808 | 11/1992 |
| WO | WO 94/12650 | 6/1994 |
| WO | WO 99/61064 | 12/1999 |

OTHER PUBLICATIONS

Ausebel et al., (Eds.), "Protocols in Molecular Biology," John Wiley & Sons (1994), pp. 6.0.3 to 6.4.10.
Capecchi, "Altering the Genome by Homologous Recombination," Science, 244:1288–1291 (1989).
Darnell, et al., (Eds.), "Molecular Cell Biology," Scientific American Books, Inc., New York, NY, 251–258 (1986).
Friedmann, "Progress Toward Human Gene Therapy," Science, 244:1275–1281 (1989).
Gibson and Shillitoe, "Ribozymes Their Functions and Strategies for Their Use," Mol. Biotech., 7:125–137 (1997).
Goodman and Gilman, (Eds.), "The Pharmacological Basis of Therapeutics," Eighth Edition, Pergamon Press, New York, 1230–1232 (1990).
Harlow and Lane, (Eds.), "Antibodies: A Laboratory Manual," Cold Spring Harbor Laboratory, Cold Spring Habor, New York (1988), Chapter 9.
Haukanes et al., "Mechanism of Incision by and Apurinic/Apyrimidinic Endonuclease Present in Human Placenta," Nucl. Acids. Res., 17:5529–35 (1999).
Hoss et al., "A Human DNA Editing Enzyme Homologous to the *Eschurichia coli* DnaQ/MutD Protein," EMBO, 18:3868–3875 (1999).
International Search Report, Patent Cooperation Treaty, PCT/US99/10578, Sep. 10, 1999.
International Search Report, patent Cooperation Treaty, PCT/US99/10578, Dec. 7, 1999.

Koonin, "A conserved Ancient Domain Joines the Growing Superfamily of 3'–5' Exonuclease," Curr. Biol., 7:R604–R606 (1997).
Lavrosky et al., "Therapeutic Potential and Mechanism of Action of Oligonucleotides and Ribozymes," Biochem. Mol. Med., 62:11–22 (1997).
Lee et al., "Generation of cDNA Probes Directed by Amino Acid Sequence: Cloning of Urate Oxidase," Science, 239:1288–91 (1988).
Lee et al., "Mechanism of Inhibition of Deoxyribonucleic Acid Synthesis by 1–B–D–Arabinofuranosyladenosine Triphosphate and Its Potentiation by 6–Mercaptopurine Ribonucleoside 5'–Monophosphate," Biochemistry, 19:215–19 (1980).
Mazur and Perrino, "Cloning of Expression of a Novel Human DNA Repair 3'–5' Exonuclease," (Abstract A–24), Proceedings American Association for Cancer Research, Endogenous Sources of Mutations, Fort Myers (1998).
Mazur and Perrino, "Identification and Expression of the TREX1 and TREX2 cDNA Sequences Encoding Mammalian 3'–5' Exonucleases," J. Biol. Chem., 274:19655–19660 (Jul. 1999).
Miller, "Human Gene Therapy Comes of Age," Nature, 357:455–460 (1992).
Nordsiek et al., GenBank Accession No. AF002998.
Parsonage et al., "Purification and Analysis of Streptococcal NADH Peroxidase Expressed in *Escherichia coli*," J. Biol. Chem., 268:3161–67 (1993).
Perrino et al.,"Exonucleases and the Incorporation of Aranucleotides into DNA," Cell Biochem. Biophys., 30:331–352 (1999).
Perrino et al., "Identification of a 3'–5'–Exanuclease That Removes Cytosine Arabinoside Monophosphate from 3' Termini of DNA," J. Biol. Chem., 269:16357–16363 (1994).
Sambrook et al., (Eds.), "Molecular Cloninig: A Laboratory Manual," Cold Spring Harbor Laboratory Press: Cold Spring Harbor, New York (1989) pp. 9.47–9.51.
Skalski et al., "Removal of Anti–Human Immunodeficiency Virus 2',3'–Dideoxynucleoside Monophosphates from DNA by a Novel Human Cytosolic 3'–5' Exonuclease," Biochem. Pharmacol., 50(6):815–21 (1995).
Verma, "Treatment of disease by introducing healthy genes into the body is becoming feasible. But the therapy will not reach its full potential untill the genes can be coaxed to work throughout life," Scientific America, 68–72, 81–84 (1990).
Zimm et al., "Cellular Pharmacokinetics of Mercaptopurine in Human Neoplastic Cells and Cell Lines," Cancer Res. 45:4156–4161 (1985).

*Primary Examiner*—Charles L. Patterson, Jr.
(74) *Attorney, Agent, or Firm*—Vinson & Elkins L.L.P.

(57) ABSTRACT

An isolated nucleic acid molecule encodes the genomic sequence encoding a human 3'–5' exonuclease. A human exonuclease independent of DNA polymerase is produced in host cells from recombinant vectors. Methods of use include inhibition of exonuclease activity to increase incorporation of nucleotide analogs into DNA in rapidly dividing cells.

14 Claims, No Drawings

HUMAN GENE ENCODING 3'-5' EXONUCLEASE

This application is a continuation of U.S. Provisional Application No. 60/148,018, filed Aug. 10, 1999 now abandoned, and U.S. Provisional Application No. 60/147,985, filed Aug. 9, 1999 also abandoned.

BACKGROUND OF THE INVENTION

There are a growing number of antineoplastic and antiviral agents such as the nucleoside analogs and dideoxy nucleosides that act as anti-metabolites by inhibiting nucleic acid polymerization, or elongation. Some resistance or ineffectiveness of these agents may be due to an exonuclease activity that removes the analog from the nucleic acid molecule and permits the analog to be replaced with the correct nucleoside.

As an example of such a therapy for treatment of acute myeloblastic leukemia (AML) includes administration of 1-β-D-arabinofuranosylcytosine (araC), an analog of dCTP and potent inhibitor of DNA replication. For a review, see Gilman, et al. (Eds.), *The Pharmacological Basis of Therapeutics*, Eighth Edition, Pergamon Press; New York (1990), pp. 1230–1232. Despite the well established therapeutic value of araC, the precise mechanism by which cell death is induced is unclear. One possibility is that inhibition of DNA synthesis without concomitant suppression of RNA and protein synthesis leads to "unbalanced growth" resulting in increased cell volume and ultimately cell death. In araC treatment, it has been observed that a large number of AML patients are initially refractory to the drug or later develop resistance to araC resulting in failure of therapy in the long term. It is believed that araC resistance arises in part from the relative activities of metabolic enzymes that participate in conversion of araC to araCTP and ultimately to an inactive araUMP. Other factors which may influence araC efficacy include (i) the ability of cells to transport araC, (ii) deoxycytidine kinase deficiency, (iii) increased CTP synthase activity which gives rise to increased intracellular dCTP that may inhibit araC activity, (iv) cytidine deaminase activity, and/or (v) coordinated polymerase/exonuclease activities. Changes in araC structure and/or intracellular concentration relative to analogous compounds may alter affinity of DNA polymerases for araC, thereby resulting in decreased incorporation of the analog into replicating DNA and decreased efficacy of araC chemotherapy regimens.

Thus there exists a need in the art to identify metabolic factors which modulate the ability of chemotherapeutic agents to effect cell killing. Isolation of polypeptides, and their underlying polynucleotide sequences that modulate araC activity would permit the design and identification of therapeutics that regulate the biological activity of the polypeptides and increase efficiency of chemotherapeutic agent at lower doses. Treatment regimens including lower doses of a chemotherapeutic agent may be more easily tolerated in patients, reduce unpleasant side effects, and increase overall efficiency of the treatment program.

SUMMARY OF THE INVENTION

The present invention addresses certain shortcomings in the fields of anti-cancer and anti-viral therapies by providing isolated 3'-5' exonucleases that are not linked to any polymerase activity, and that are shown herein to be involved in decreasing the effectiveness of certain therapeutic compounds, and in particular by providing an isolated human genomic 3'-5' exonuclease encoding polynucleotide. For example, agents such as nucleoside analogs and chain-terminating dideoxynucleotides, which are used as therapeutic agents against proliferating cells, are removed from a cellular or viral genome by the disclosed exonucleases during treatment, allowing the cell or virus to continue to proliferate. In light of the present disclosure, these isolated exonucleases may be inhibited or even eliminated from a cell containing an anti-proliferative therapeutic agent in order to increase the effectiveness of such an agent.

Disclosed herein are isolated nucleic acid molecules of from about 708 to about 1642 nucleotides in length that include a gene, or the full length complement of a gene, particularly genes that encode a polypeptide, or protein, that includes the amino acid sequence of those sequences designated herein as SEQ ID NO:2, SEQ ID NO:4, SEQ ID 30, SEQ ID NO:32 or SEQ ID NO:34 and conservative variants of these polypeptides. Conservative variants of a polypeptide typically contain an alternative amino acid at one or more sites within the protein. Substitutions preferably are conservative, that is, one amino acid is replaced with one of similar size and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Conservative variants may also include small deletions or insertions of amino acids, so long as the protein maintains its enzymatic activity.

For example, insertional variants may include fusion proteins such as those used to allow rapid purification of the polypeptide and also may include hybrid proteins containing sequences from other proteins and polypeptides such as homologues of the polypeptide. For example, an insertional variant may include portions of the amino acid sequence of the polypeptide from one species, together with portions of the homologous polypeptide from another species. Other insertional variants may include those in which additional amino acids are introduced within the coding sequence of the polypeptide. These typically are smaller insertions than the fusion proteins described above and are introduced, for example, to disrupt a protease cleavage site, or to aid in chromatographic purification of the polypeptide.

Also disclosed are several regions, hereinafter conserved regions, within these amino acid sequences that are evolutionarily conserved between the human, murine and Drosophila polypeptides or proteins. For example, in one particular region of the polypeptides disclosed herein that includes a contiguous sequence from about amino acids 12 through 25 of SEQ ID NO:2, about amino acids 8 through 21 of SEQ ID NO:4, about amino acids 12 through 25 of SEQ ID NO:30, about amino acids 8 through 21 of SEQ ID NO:32 and about amino acids 18 through 31 of SEQ ID NO:34 is substantially conserved between these three species and may be so among other species as well. Additionally, a second region of conserved amino acid sequence is disclosed herein to be from about amino acid 124 through about 134 of SEQ ID NO:2, from about amino acid 113 or about 117 through about 127 of SEQ ID NO:4, from about amino acid 120 or 124 through about 134 of SEQ ID NO:30, from about amino acid 117 through about 127 of SEQ ID NO:32 and from about amino acid 129 or 133 through about 143 of SEQ ID NO:34 is substantially conserved between these three species and may be so among others. Furthermore, a third region from about amino acids 195 through 205 of SEQ ID NO:2, 188 through 198 of SEQ ID NO:4, 195 through 205 of SEQ ID NO:30, 188 through 198 of SEQ ID NO:32 and 303 through 313 of SEQ ID NO:34 is also conserved among the three species and may be conserved among other species. The disclosed invention also encompasses mutations of the conserved regions which may be conservative in nature, or may be targeted to disrupt or modify enzymatic activity of the polypeptides or may be targeted to disrupt or modify potential interactions with other molecules.

In certain embodiments, the polypeptides or proteins disclosed herein are encoded by the nucleic acid sequences designated herein as SEQ ID NO:1, SEQ ID NO:3, SEQ ID NO:29, SEQ ID NO:31, SEQ ID NO:33 or the complement, or full length complement of any of these. As used herein the term "complement" is used to define a second strand of nucleic acid that will hybridize to a first nucleic acid sequence to form a double stranded molecule under highly stringent conditions. Highly stringent conditions are those that allow hybridization between two nucleic acid sequences with a high degree of homology, but precludes hybridization of random sequences. For example, hybridization at low temperature and/or high ionic strength is termed low stringency and hybridization at high temperature and/or low ionic strength is termed high stringency. In a general sense, a low stringency hybridization may include conditions of 0.15 M to 0.9 M NaCl at a temperature range of 20° C. to 50° C. High stringency may generally include conditions of 0.02 M to 0.15 M NaCl at a temperature range of 50° C. to 70° C. Preferred nucleic acid segments as disclosed herein are those that hybridize to the nucleic acid sequences designated herein as SEQ ID NOS:1, 3, 29, 31 or 33 under conditions including hybridization at 50° C. in 1×SSC, and washing at 65° C. in 0.1×SSC. As known in the art, 1×SSC is a solution containing about 8.76 grams/liter NaCl and about 4.41 grams/liter sodium citrate. The temperature and ionic strength of a desired stringency are understood to be applicable to particular probe lengths, to the length and base content of the sequences and to the presence of formamide, tetramethylammonium chloride or other solvents in the hybridization mixture. It is also understood that these ranges are mentioned by way of example only, and that the desired stringency for a particular hybridization reaction is often determined empirically by comparison to positive and negative controls. To hybridize is understood to mean the forming of a double stranded molecule or a molecule with substantial double stranded nature.

Equations have been derived to relate duplex formation to the major variables of temperature, salt concentration, nucleic acid strand length and composition, and formamide concentration.

Eg:

$$Tm = 81.5 - 16.6(\log[Na^+]) + 0.41(\%GC) - 600/N \quad 1.$$

(Tm=temperature for duplex to half denature; N=chain length $$Tm = 81.5 - 16.6(\log[Na^+]) + 0.41(\%GC) - 0.63(\% \text{ formamide}) - 600/N \quad 2.$$

One can thus predict whether complementary strands will exist in double-stranded or single-stranded form under a given set of conditions, and can determine high stringency conditions based on knowledge of the nucleotide sequences.

It is understood in the art that a nucleic acid sequence will hybridize with a complementary nucleic acid sequence under high stringency conditions even though some mismatches may be present. Such closely matched, but not perfectly complementary sequences are also encompassed by the present invention. For example, differences may occur through genetic code degeneracy, or by naturally occurring or man made mutations and such mismatched sequences would still be encompassed by the present disclosure. A complement may also be described, therefore, as a fragment of DNA (nucleic acid segment) or a synthesized single stranded oligomer that may contain small mismatches or gaps when hybridized to its complement, but that is able to hybridize to the complementary DNA under high stringency conditions. The full length complement is understood to indicate that the two molecules hybridize along the full length of the gene or complementary region. For example the full length complement of a gene would be a complementary molecule that is complementary along the entire gene rather than complementary to only a small portion of the gene. It is also understood that a nucleic acid strand that includes the full length complement of a gene may also contain extraneous nucleotides flanking the complementary region, or linked to either end of the complementary region and such strands would still be defined as the full length complement of the gene. Furthermore, it is understood that the portions of SEQ ID NO:1, SEQ ID NO:3, SEQ ID NO:29, SEQ ID NO:31 and SEQ ID NO:33 that encode the conserved regions would be particularly useful in the identification of other exonucleases either intra- or inter-species searches. The present invention also encompasses the use of degenerate probes targeted to said conserved regions.

The nucleic acid molecules disclosed herein are, in certain embodiments, operatively linked to a promoter, and may be operatively linked to the autogenous promoter for that gene or to a heterologous promoter, and may be linked to any appropriate promoter known in the art that is appropriate for the particular application. For example, certain promoters may be chosen for expression in a particular type of cell, or for high expression, or even for inducible expression of the gene of interest. The selection of such promoters is well known and routine in the art, and a comprehensive list of all available promoters is available from various sources to those in the art. In certain embodiments the gene will be operatively linked to its own (autogenous) promoter, either as the promoter is present in a cell, or with nucleic acid sequence added to, or removed from the nucleic acid molecule between the promoter region and the translational start site. A preferred promoter for use in the present invention may be, for example, a promoter contained in the nucleic acid sequence designated herein as SEQ ID NO: 1, in particular those sequences from about base 9 to about base 59, or from about base 519 to about base 569 of SEQ ID NO:1. A gene as disclosed herein may also be linked to various markers known in the art to monitor transformation efficiency or to otherwise detect the presence of the gene. Such markers are also routine and known in the art.

The nucleic acids of the present disclosure may also be contained in a vector. A vector used in the practice of the invention may be a plasmid, a viral vector, and also may be an expression vector that directs expression of the disclosed genes in an appropriate host cell. Vectors as described herein may be compatible with certain host cells such as bacterial cells, yeast, plant, animal, or even mammalian cells. Certain aspects of the disclosure may also include vectors contained in host cells.

In certain embodiments, the present disclosure encompasses compositions containing purified or partially purified proteins or polypeptides. Such partially purified polypeptides having a 3'–5' exonuclease activity, include those having or including the amino acid sequences designated herein as SEQ ID NO:2, SEQ ID NO:4, SEQ ID NO:30, SEQ ID NO:32 or SEQ ID NO:34 or a conservative variant of any thereof. A polypeptide as disclosed herein may be a naturally occurring protein that is isolated from a cell, such as a mammalian cell or even a mouse or human cell, using chromatographic or other techniques as disclosed herein or known in the art. Such techniques generally include isolation of a particular fraction of a cell culture, such as the aqueous fraction, for example, and a protein precipitation in the presence of an ammonium salt, such as ammonium sulfate.

Polypeptides as disclosed herein may also be recombinant proteins or polypeptides expressed from a manmade vector or isolated gene. Such recombinant proteins may also be isolated from a cell culture as described for the naturally occurring proteins, but are often "overexpressed" at a higher level than normal.

As such, a method for producing a polypeptide having 3'-5-exonuclease activity is also disclosed herein. Such a method may include obtaining a nucleic acid molecule including a gene encoding a polypeptide including the sequence of SEQ ID NO:2, SEQ ID NO:4, SEQ ID NO:30, SEQ ID NO:32 or SEQ ID NO:34 or a conservative variant of any thereof, operatively linked to a promoter sequence; transferring the nucleic acid molecule into a host cell; and growing the host cell under conditions effective to express the gene. In certain embodiments, the method may further include isolating the polypeptide from a host cell or from the medium of its growth. It is also understood that in certain embodiments a recombinantly produced protein may be used in the intracellular compartment where it is expressed, in a candidate screening assay for example, and such methods would not require isolation of the protein product. Proteins and polypeptides of the invention may be produced in any appropriate cell, including but not limited to, bacterial cells and eukaryotic cells such as mammalian cells.

The present disclosure also encompasses antibodies specifically immunoreactive with a polypeptide that includes the amino acid sequence of SEQ ID NO:2, SEQ ID NO:4, SEQ ID NO:30, SEQ ID NO:32 or SEQ ID NO:34 and more particularly, antibodies with specific reactivity to the conserved regions described above. Antibodies may be polyclonal or monoclonal antibodies, although monoclonal antibodies are preferred for certain embodiments, and may also include anti-idiotype antibodies specifically immunoreactive with the disclosed antibodies.

An aspect of the present disclosure is a method of identifying an effector of a 3'-5' exonuclease activity. This method includes obtaining a candidate substance; contacting a 3'-5' exonuclease polypeptide composition with a substrate in the presence and absence of the candidate substance; and detecting 3'-5' exonuclease activity in the presence and absence of the candidate substance; wherein a change in activity of the exonuclease in the presence of the candidate substance is indicative of an effector of 3'-5' exonuclease activity. Also encompassed herein are effectors of 3'-5' exonuclease activity identified by this method, and pharmaceutical compositions including such an effector. An effector of exonuclease activity may be an activator or an inhibitor of the enzymatic activity, or even of the expression of the protein in a cell. Furthermore, an effector of 3'-5' exonuclease activity might be a variant form of an exonuclease peptide itself with or without exonuclease activity.

A method of identifying an inhibitor of 3'-5' exonuclease activity may include obtaining a candidate substance; growing a cell culture in the presence of a nucleoside analog that is incorporated into a nucleic acid molecule and inhibits polymerization of the molecule when incorporated therein, wherein the cells express a 3'-5-exonuclease activity; contacting the cell culture with the candidate substance; growing an identical cell culture that is not contacted with the candidate substance; and comparing the cell growth in the presence and absence of the candidate substance; wherein a decrease in cell growth in the presence of the candidate substance is indicative of an inhibitor of 3'-5' exonuclease activity. It is an aspect of the present disclosure that an effector of the 3'-5' exonuclease activity may either interact with a 3'-5' exonuclease protein and inhibit its activity through direct contact, or a substance may inhibit the expression of a gene encoding the 3'-5' exonuclease protein through interaction with the promoter or other control sequence, or even with a portion of the coding sequence of the gene, such as an antisense molecule, for example. As such, both an effector of the protein product, and an effector of genetic expression of the protein product are aspects of the present disclosure, and would be useful in the practice of the present invention.

A screening assay as described herein may include obtaining a candidate substance, which can come from any source. For example, it is proposed that compounds isolated from natural sources such as fungal extracts, plant extracts, bacterial extracts, higher eukaryotic cell extracts, or even extracts from animal sources, or marine, forest or soil samples, may be assayed for the presence of potentially useful pharmaceutical agents. In addition, man made or synthetic substances which would include, but are not limited to, nucleic acid analogs, peptides, polypeptides or other compounds designed de novo based on the predicted protein structure of the exonuclease enzyme, may also be screened for possible use as pharmaceutical agents, or as agents to be used in combination with other pharmaceutical agents. It is also understood that antibodies and other isolated or purified, but naturally occurring compounds, could be screened by this process. The active compounds may include fragments or parts of naturally-occurring compounds or may be only found as active combinations of known compounds which are otherwise inactive.

The present disclosure also includes methods of inhibiting the replication of a nucleic acid molecule in a cell that expresses a 3'-5' exonuclease activity comprising contacting said cell with a nucleic acid polymerization inhibitor such as a nucleoside analog or a dideoxy nucleotide, and further contacting the cell with an inhibitor of the 3'-5' exonuclease activity. This method may preferably be practiced in any type of cell, including, but not limited to, a mammalian cell, a human cell, or even a human cancer cell. The method is particularly advantageous when applied to a proliferating tumor or cancer cell, or a virally infected cell, such as a mammalian cell infected with a virus, and including T-cells and monocyte/macrophage. Viruses would include, but not be limited to, retroviruses including HIV, herpes simplex viruses (1 and 2), Epstein-Barr viruses, varicella-zoster viruses, influenza viruses, Lassa fever, infectious hepatitis, dengue fever, measles, respiratory syncytial viruses, vaccinia viruses, and cytomegaloviruses, for example. As a part of this method, one may include any dideoxynucleotide, such as ddATP, ddGTP, ddCTP, ddUTP, ddTTP or even ddITP, and may also include nucleoside analogs, and compounds that are converted to nucleoside analogs in the cell. Such drugs would include cytarabine, fluorouracil, mercaptopurine, thioguanine, acyclovir, didanosine, ganciclovir sodium, idoxuridine, ribavirin, trifluridine, zalcitabine, azacitidine, and zidovudine, for example.

Also disclosed are methods of identifying a compound as a specific binding partner of the exonuclease polypeptide. In a preferred method, the specific binding partner modulates activity of the exonuclease polypeptide. In a most preferred embodiment, the methods of the invention identify compounds that inhibit biological activity of the exonuclease polypeptide. It is contemplated that compounds that interact with active site amino acids, such as amino acids 2 through 17, 111 through 125, or 181 through 196 of SEQ ID NO:2, or amino acids 8 through 24, 114 through 128, or 184 through 199 of SEQ ID NO:4 may be particularly useful. In addition, it is contemplated that compounds which interact with the conserved regions, individually or in combination, of SEQ ID NO:2, SEQ ID NO:4, SEQ ID NO:30, SEQ ID NO:32 or SEQ ID NO:34 would also be particularly useful.

The invention also provides methods to identify an inhibitor compound of an exonuclease biological activity comprising the steps of a) contacting the exonuclease polypeptide encoded by a polynucleotide of the invention with a substrate in the presence and absence of a test compound; b) comparing biological activity of the exonuclease polypeptide in the presence and absence of the test compound; and c) identifying the test compound as an inhibitor compound when biological activity of the exonuclease polypeptide is decreased in the presence of the test compound. Also provided are inhibitors identified by the method and pharmaceutical compositions comprising an inhibitor identified by the method of the invention.

It is a further aspect of the invention that one may obtain a genetic construct containing a promoter region, or a control region of the 3'–5' exonuclease, and particularly a human TREX1 gene promoter, such as a promoter region contained in SEQ ID NO:1, or another promoter that may be isolated from the human or other animal genome using the sequence, or fragments of the sequence disclosed herein as SEQ ID NO:1. Such a construct will contain an encoded gene operatively linked to the promoter region such that the gene is under the transcriptional control of the promoter region. In certain embodiments the encoded gene will be a gene encoding a 3'–5' exonuclease and in certain embodiments a gene encoding a reporter gene may be included. Such reporter genes would include, but would not be limited to a luciferase gene, an antibiotic resistance marker, or an essential metabolic gene, a β-galactosidase gene from *E. coli* or a chloramphenicol acetyltransferase gene, for example. In this embodiment, the reporter gene would be expressed in the presence and absence of a candidate substance as in the previously described screening assays. A change in level of the reporter gene product in the presence of the candidate substance relative to the level in the absence of the candidate substance would indicate an effector of 3'–5' exonuclease expression.

An increase in reporter gene activity over a control would indicate an activating substance and a decrease in activity over the control would indicate an inhibitor. It is understood that, in the assays described herein, the inhibition of 3'–5' exonuclease activity in a cell could occur at any level of the expression of 3'–5' exonuclease activity, including gene transcription, RNA processing, mRNA translation, post translational modification and even protein transport or at any other level that would have the overall effect of activation or inhibition of 3'–5' exonuclease activity, and that the methods described and claimed would include effectors at any of these, or any other level of protein expression. Preferred cells to be used in the assay would be Chinese hamster ovary cells (CHO) for example, however, any cells which are capable of expressing a 3'–5' exonuclease, or a reporter gene as described herein would be acceptable and would be encompassed by the present claimed invention. Examples of other cell types include MDCK, CaCo$_2$, BHK, COS AND 293 cells, for example.

The invention further provides methods for increasing incorporation of a nucleotide analog into replicating DNA in a cell comprising the steps of, a) contacting the cell with a nucleotide analog, and b) contacting the cell with an inhibitor of an exonuclease polypeptide activity encoded by a polynucleotide as disclosed herein. In a preferred method, the exonuclease is selected from the group consisting of TREX1h, TREX2h, TREX1m, or TREX2m. The inhibitor may be a substrate analog, an antibody, an antisense molecule, or another exonuclease peptide with or without exonuclease activity, or an inhibitor of either gene expression or enzymatic activity. An inhibitor may be included in a pharmaceutical composition including a nucleotide analog such as araC, or chain terminating nucleotide such as a dideoxy nucleotide, or it may be administered separately.

DETAILED DESCRIPTION

The present invention provides polypeptides and underlying polynucleotides for a novel exonuclease family of proteins exemplified by human and mouse 3'–5' exonucleases, termed by the inventor TREX1h, TREX2h, TREX1m, TREX2m and TREXDm and more particularly to an isolated human genomic TREX1h nucleic acid segment. Although the previous work of the present inventor had indicated that the full length TREX1h gene had been isolated from cDNA, it is the surprising discovery, disclosed herein, that the human gene encodes an additional 10 amino acids at the N-terminus of the previously reported protein. This discovery was found only by using human genomic DNA as a target for gene cloning using the sequences discovered as described herein below.

The invention includes both naturally occurring and non-naturally occurring exonuclease polynucleotides and polypeptide products thereof. Naturally occurring exonuclease products include distinct gene and polypeptide species within the exonuclease family. These species include those that are expressed within cells of the same animal as well as corresponding species homologs expressed in cells of other animals. Within each exonuclease species, the invention further provides splice variants encoded by the same polynucleotide but which arise from distinct mRNA transcripts. Non-naturally occurring exonuclease products include variants of the naturally occurring products with or without exonuclease activity such as analogs and exonuclease products altered through covalent modifications.

In a preferred embodiment, the invention provides polynucleotides encoding exonucleases comprising the sequences set forth in SEQ ID NOS:1, 3, 29, 31 and 33. The invention also embraces polynucleotides encoding the amino acid sequences set out in SEQ ID NOS:2, 4, 30, 32 and 34. A presently preferred polypeptide of the invention comprises the amino acid sequences set out in SEQ ID NO:2, which is the protein encoded by the human genomic copy of the gene.

The present invention provides novel purified and isolated polynucleotides (e.g., DNA sequences and RNA transcripts, both sense and complementary antisense strands, including splice variants thereof) encoding the human, mouse and Drosophila exonucleases. DNA sequences of the invention include genomic and cDNA sequences as well as wholly or partially chemically synthesized DNA sequences. "Synthesized," as used herein and is understood in the art, refers to purely chemical, as opposed to enzymatic, methods for producing polynucleotides. "Wholly" synthesized DNA sequences are, therefore, produced entirely by chemical means, and "partially" synthesized DNAs embrace those wherein only portions of the resulting DNA were produced by chemical means. A preferred DNA sequence encoding a genomic human TREX1h (Exo 1) polypeptide is set out in SEQ ID NO:1, a preferred DNA sequence encoding a human TREX2h (Exo2h) polypeptide is set out in SEQ ID NO:3, a preferred DNA sequence encoding a murine TREX1m polypeptide is set out in SEQ ID NO:29, a preferred DNA sequence encoding a murine TREX2m polypeptide is set out in SEQ ID NO:31 and a preferred DNA sequence encoding a Drosophila melanogaster TREXDm polypeptide is set out in SEQ ID NO:33. The worker of skill in the art will readily appreciate that the preferred DNAs of the invention comprise a double stranded molecule, for example, the molecule having the sequence set forth in SEQ ID NO:1 along with the complementary molecule (the "non-coding strand" or "complement") having a sequence deducible from the sequence of SEQ ID NO:1 according to Watson-Crick base pairing rules for DNA. Also preferred are polynucleotides encoding the polypeptides of SEQ ID NOS:2, 4, 30, 32 and 34. The invention further embraces species, preferably mammalian, homologs of the human exonuclease DNA's.

The invention also embraces polynucleotide sequences encoding exonuclease species that exhibit greater than 45% identity to the polynucleotide set out in SEQ ID NO:1 or to any or all of the conserved regions as defined above and hybridize under highly stringent conditions to the non-coding strand, or complement, of the polynucleotides in SEQ ID NO:1. Identity herein is determined using GAP program alignment (GCG software) with parameters of (i) gap weight 50, (ii) length weight 3, (iii) average match 10.0, and (iv) average mismatch 0.0. The worker of ordinary skill will realize that other methods for determining identity can easily be applied under conditions/parameters similar to those described herein. DNA sequences encoding exonuclease polypeptides that would hybridize thereto but for the redundancy of the genetic code are contemplated by the invention. Exemplary highly stringent hybridization conditions are as follows: hybridization at 50° C. in 1×SSC, and washing at 65° C. in 0.1×SSC. It is understood in the art that conditions of equivalent stringency can be achieved through variation of temperature and buffer, or salt concentration as described Ausebel, et al. (Eds.), *Protocols in Molecular Biology*, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), *Molecular Cloning: A Laboratory Manual*, Cold Spring Harbor Laboratory Press: Cold Spring Harbor, N.Y. (1989), pp. 9.47 to 9.51.

Autonomously replicating recombinant expression constructions such as plasmid and viral DNA vectors incorporating exonuclease-encoding sequences are also provided. Expression constructs wherein exonuclease-encoding polynucleotides are operatively linked to an endogenous or exogenous expression control DNA sequence and a transcription terminator are also provided. The genes can be expressed in any number of different recombinant DNA expression systems to generate large amounts of the polypeptide product, which can then be purified and used to vaccinate animals to generate antisera with which further studies may be conducted, or to screen candidate substances for inhibitors or effectors of exonuclease activity.

Examples of expression systems known to the skilled practitioner in the art include bacteria such as *E. coli*, yeast such as *Pichia pastoris*, baculovirus, and mammalian expression systems such as in COS or CHO cells. A complete gene can be expressed or, alternatively, fragments of the gene encoding portions of polypeptide can be produced.

The gene or gene fragment encoding a polypeptide may be inserted into an expression vector by standard subcloning techniques. An *E. coli* expression vector may be used which produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.).

Some of these systems produce recombinant polypeptides bearing only a small number of additional amino acids, which are unlikely to affect the antigenic ability of the recombinant polypeptide. For example, both the FLAG system and the 6×His system add only short sequences, both of which are known to be poorly antigenic and which do not adversely affect folding of the polypeptide to its native conformation. Other fusion systems are designed to produce fusions wherein the fusion partner is easily excised from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

The expression system used may also be one driven by the baculovirus polyhedron promoter. The gene encoding the polypeptide may be manipulated by standard techniques in order to facilitate cloning into the baculovirus vector. One baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant antigen. See Summers et al., A Manual of Methods for Baculovirus Vectors and Insect Cell Culture Procedures, Texas Agricultural Experimental Station; U.S. Pat. No. 4,215,051 (incorporated by reference).

Major antigenic determinants of the polypeptide may be identified by an empirical approach in which portions of the gene encoding the polypeptide are expressed in a recombinant host, and the resulting proteins tested for their ability to elicit an immune response. For example, PCR may be used to prepare a range of peptides lacking successively longer fragments of the C-terminus of the protein. The immunoprotective activity of each of these peptides then identifies those fragments or domains of the polypeptide which are essential for this activity. Further studies in which only a small number of amino acids are removed at each iteration then allows the location of the antigenic determinants of the polypeptide.

A method that may be used for the preparation of the polypeptides as disclosed herein is the use of peptide mimetics. Mimetics are peptide-containing molecules which mimic elements of protein secondary structure. See, for example, Johnson et al., "Peptide Turn Mimetics" in *BIOTECHNOLOGY AND PHARMACY*, Pezzuto et al, Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

The nucleic acid sequences disclosed herein may be expressed as encoded peptides or proteins. The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

Both cDNA and genomic sequences are suitable for eukaryotic expression, as the host cell will generally process the genomic transcripts to yield functional mRNA for translation into protein. In addition, it is possible to use partial sequences for generation of antibodies against discrete portions of a gene product, even when the entire sequence of that gene product remains unknown. Computer programs are available to aid in the selection of regions which have potential immunologic significance. For example, software capable of carrying out this analysis is readily available commercially, for example MacVector (IBI, New Haven, Conn.). The software typically uses standard algorithms such as the Kyte/Doolittle or Hopp/Woods methods for locating hydrophilic sequences which are characteristically found on the surface of proteins and are, therefore, likely to act as antigenic determinants.

As used herein, the terms "engineered" and "recombinant" cells are intended to refer to a cell into which an exogenous DNA segment or gene, such as a cDNA or gene has been introduced through the hand of man. Therefore, engineered cells are distinguishable from naturally occurring cells which do not contain a recombinantly introduced exogenous DNA segment or gene. Recombinant cells include those having an introduced cDNA or genomic gene, and also include genes positioned adjacent to a heterologous promoter not naturally associated with the particular introduced gene.

To express a recombinant encoded protein or peptide, whether mutant or wild-type, in accordance with the present invention one would prepare an expression vector that comprises one of the claimed isolated nucleic acids under the control of, or operatively linked to, one or more promoters. To bring a coding sequence "under the control of" a promoter, or to "operatively link to a promoter," one positions the 5' end of the transcription initiation site of the transcriptional reading frame generally between about 1 and about 50 nucleotides "downstream" (i.e., 3') of the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as $E.$ $coli$ and $B.$ $subtilis$ transformed with recombinant bacteriophage DNA, plasmid DNA or cosmid DNA expression vectors.

Certain examples of prokaryotic hosts are $E.$ $coli$ strain RR1, $E.$ $coli$ LE392, $E.$ $coli$ B, $E.$ $coli$ X 1776 (ATCC No. 31537) as well as $E.$ $coli$ W3 110 (F-, lambda-, prototrophic, ATCC No. 273325); bacilli such as $Bacillus$ $subtilis$; and other enterobacteriaceae such as $Salmonella$ $typhimurium$, $Serralia$ $inarcescens$, and various Pseudomonas species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, $E.$ $coli$ is often transformed using pBR322, a plasmid derived from an $E.$ $coli$ species. pBR322 contains genes for ampicillin and tetracycline resistance and thus provides easy means for identifying transformed cells. The pBR plasmid, or other microbial plasmid or phage must also contain, or be modified to contain, promoters which may be used by the microbial organism for expression of its own proteins.

In addition, phage vectors containing replicon and control sequences that are compatible with the host microorganism may be used as transforming vectors in connection with these hosts. For example, the phage lambda GEM™-11 may be utilized in making a recombinant phage vector which may be used to transform host cells, such as $E.$ $coli$ LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cells lines or host systems may be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons may be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells may be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn may be cloned and expanded into cell lines.

A number of selection systems may be used, including but not limited to, the herpes simplex virus thymidine kinase, hypoxanthine-guanine phosphoribosyltransferase, and adenine phosphoribosyltransferase genes, in tk-, hgprt- or aprt-cells, respectively. Also, antimetabolite resistance may be used as the basis of selection for dhfr, that confers resistance to methotrexate; gpt, that confers resistance to mycophenolic acid; neo, that confers resistance to the aminoglycoside G-418; and hygro, that confers resistance to hygromycin.

It is contemplated that the isolated nucleic acids of the invention may be "overexpressed", i.e., expressed in increased levels relative to its natural expression, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

According to an aspect of the invention, therefore, host cells are provided that include prokaryotic and eukaryotic cells, either stably or transiently transformed with DNA sequences of the invention in a manner that permits expression of exonuclease polypeptides of the invention. Host cells are a valuable source of immunogen for development of antibodies specifically immunoreactive with exonuclease polypeptides of the invention. Host cells are also conspicuously useful in methods for large scale production of exonuclease polypeptides wherein the cells are grown in a suitable culture medium and the desired polypeptide products are isolated from the cells or from the medium in which the cells are grown by, for example, immunoaffinity purification.

Knowledge of exonuclease DNA sequences allows for modification of cells to modulate expression of endogenous exonuclease polypeptides of the invention. Cells can be modified (e.g., by homologous recombination) to provide increased exonuclease expression by replacing, in whole or in part, the naturally occurring exonuclease promoter with all or part of a heterologous promoter so that the cells express, for example, TREX 1h at higher levels. The heterologous promoter is inserted in such a manner that it is operatively-linked to exonuclease encoding sequences. See, for example, PCT International Publication No. WO 94/12650, PCT International Publication No. WO 92/20808, and PCT International Publication No. 91/09955 (all incorporated herein by reference). The invention also contemplates that, in addition to heterologous promoter DNA, amplifiable marker DNA (e.g., ada, dhfr, and the multifunctional CAD gene that encodes carbamyl phosphate synthase, aspartate transcarbamylase, and dihydroorotase) and/or intron DNA may be inserted along with the heterologous promoter DNA. If linked to the exonuclease-coding sequence, amplification of the marker DNA by standard selection methods results in co-amplification of the exonuclease coding sequences in the cells.

The DNA sequence information provided by the present invention also makes possible the development through, e.g. homologous recombination or "knock-out" strategies [Capecchi, Science 244:1288–1292 (1989)], of animals that fail to express functional exonucleases of the invention or that express variants thereof. Such animals are useful as models for studying the in vivo activities of, for example, TREX1h, TREX2h, TREX1m, TREX2m, and modulators thereof.

The invention also provides purified and isolated mammalian exonuclease polypeptides. Presently preferred are a human TREX1h polypeptide comprising the amino acid sequence set out in SEQ ID NO:2, a human TREX2h polypeptide comprising the amino acid sequence set out in SEQ ID NO:4, a murine TREX1m polypeptide comprising the amino acid sequence set out in SEQ ID NO:30, a murine TREX2m polypeptide comprising the amino acid sequence set out in SEQ ID NO:32, a *D. melanogaster* TREXDm comprising the amino acid sequence set out in SEQ ID NO:34 and polypeptides containing conserved regions as defined herein. Exonuclease polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention. Exonuclease products of the invention may be full length polypeptides, biologically active fragments, or variants thereof that retain specific exonuclease biological or immunological activity. Variants may comprise exonuclease polypeptide analogs wherein one or more of the specified (i.e., naturally encoded) amino acids is deleted or replaced or wherein one or more non-specified amino acids are added: (1) without loss of one or more of the biological activities or immunological characteristics specific for exonuclease polypeptides of the invention; or (2) with specific disablement of a particular biological activity of an exonuclease of the invention. Preferred fragments of the invention represent catalytic regions of polypeptides of the invention and include polypeptides comprising amino acid residues 12 through 27, 121 through 135, and 181 through 195 as set out in SEQ ID NO 2 for TREX1h and polypeptides comprising amino acid residues 8 through 24, 114 through 128, and 174 through 187 as set out in SEQ ID NO:4, the analogous residues in SEQ ID NOs:30, 32 and 34, as well as the residues comprising the conserved regions of these sequences.

Variant polypeptides include those wherein conservative substitutions have been introduced by modification of polynucleotides encoding the exonucleases. Conservative substitutions are recognized in the art to classify amino acids according to their related physical properties as defined in Table I (from WO 97/09433 published Mar. 13, 1997 (PCT/GB96/02197, filed Sep. 6, 1996, page 10). Alternatively, conservative amino acids can be grouped as defined in Lehninger, [*Biochemistry*, Second Edition-, Worth Publishers, Inc. NY, N.Y. (1975), pp.71–77] as set out in Table II. Both Tables I and II define amino acid residues by one letter abbreviations understood in the art.

TABLE 1

Conservative Substitutions I

| SIDE CHAIN CHARACTERISTIC | AMINO ACIDS |
|---|---|
| Aliphatic - Non-Polar | GAP |
|  | ILV |
| Polar - Uncharged | CSTM |
|  | NQ |
| Polar - Charged | DE |
|  | KR |
| Aromatic | HFWY |
| Other | NQDE |

TABLE II

Conservative Substitutions II

| SIDE CHAIN CHARACTERISTIC | AMINO ACID |
|---|---|
| Non-polar (hydrophobic) | |
| A. Aliphatic | ALIVP |
| B. Aromatic | FW |
| C. Sulfur containing | M |
| D. Borderline | G |
| Uncharged - polar | |
| A. Hydroxyl | STY |
| B. Amides | NQ |
| C. Sulfhydryl | C |
| D. Borderline | G |
| Positively charged (Basic) | KRH |
| Negatively charged (Acidic) | DE |

Variant products of the invention include mature exonuclease products, i.e., exonuclease products wherein leader or signal sequences are removed, those having additional amino terminal residues, or those with modified glycosylation sites. Exonuclease products having an additional methionine residue at position −1, for example, $Met^{-1}$-TREX1, are contemplated, as are exonuclease products having additional methionine and lysine residues at positions −2 and −1, for example, $Met^{-2}$-$Lys^{-1}$-TREX1. Variants of these types are particularly useful for recombinant protein production in bacterial cell types.

The invention also embraces exonuclease variants having additional amino acid residues that result from use of specific expression systems. For example, use of commercially available vectors that express a desired polypeptide such as a glutathione-S-transferase (GST) fusion product provide the desired polypeptide having an additional glycine residue at position −1 as a result of cleavage of the GST component from the desired polypeptide. Variants that result from expression in other vector systems are also contemplated.

Also comprehended by the present invention are antibodies (e.g., monoclonal and polyclonal antibodies, single chain antibodies, chimeric antibodies, CDR-grafted antibodies and the like) and other binding proteins specific for exonuclease products of the invention or fragments thereof. The term "specific for" indicates that the variable regions of the antibodies of the invention recognize and bind exonuclease polypeptides of the invention exclusively (i.e., able to distinguish TREX1h, TREX2h, TREX1m, TREX2m or TREXDm polypeptides from the family of exonuclease polypeptides despite sequence identity, homology, or similarity found in the family of polypeptides), but may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (eds), *Antibodies, A Laboratory Manual*; Cold Spring Harbor Laboratory; Cold Spring Harbor, N.Y. (1988), Chapter 6. Antibodies that recognize and bind fragments of the exonuclease polypeptides of the invention are also contemplated, provided that the antibodies are first and foremost specific for, as defined above, exonuclease polypeptides. As with antibodies that are specific for full length exonuclease polypeptides, antibodies of the invention that recognize exonuclease fragments are those that can distinguish, for example TREX1h, TREX2h, TREX1m, TREX2m or TREXDm polypeptides from the family of exonuclease polypeptides despite inherent sequence identity, homology, or similarity found in the family of proteins.

Specific binding polypeptides, and in particular antibodies, for exonuclease polypeptides of the invention can be identified, synthesized, or generated using isolated or recombinant exonuclease products, exonuclease variants, or cells expressing such products. Specific binding sequences can be useful for purifying exonuclease products and detection or quantification of exonuclease products in fluid and tissue samples using known immunological procedures. Binding proteins are also manifestly useful in modulating (i.e., blocking, inhibiting or stimulating) biological activities of exonucleases, especially those activities involved in site specific DNA binding. Anti-idiotypic antibodies specific for anti-TREX1h, anti-TREX2h, anti-TREX1m, anti-TREX2m and anti-TREXDm antibodies are also contemplated.

The DNA and amino acid sequence information provided by the present invention also makes possible the systematic analysis of the structure and function of the exonucleases of the invention. DNA and amino acid sequence information for the exonucleases also permits identification of binding partner compounds with which an exonuclease polypeptide or polynucleotide will interact. Agents that modulate (i.e., increase, decrease, or block) exonuclease activity or expression may be identified by incubating a putative modulator with an exonuclease polypeptide or polynucleotide and determining the effect of the putative modulator on exonuclease activity or expression. The selectivity of a compound that modulates the activity of the exonuclease can be evaluated by comparing its binding activity on, for example TREX1h, TREX2h, TREX1m, TREX2m or TREXDm to its activity on other exonuclease enzymes. Cell based methods, such as di-hybrid assays to identify DNAs encoding binding compounds and split hybrid assays to identify inhibitors of exonuclease polypeptide interaction with a known binding polypeptide, as well as in vitro methods, including assays wherein an exonuclease polypeptide, exonuclease-encoding polynucleotide, or a binding partner are immobilized, and solution assays are contemplated by the invention.

Selective modulators may include, for example, antibodies and other proteins or peptides that specifically bind to an exonuclease polypeptide or an exonuclease-encoding nucleic acid, oligonucleotides that specifically bind to a exonuclease polypeptide or an exonuclease gene sequence, and other non-peptide compounds (e.g., isolated or synthetic organic and inorganic molecules) that specifically react with an exonuclease polypeptide or underlying nucleic acid. Mutant exonuclease polypeptides that affect the enzymatic activity or cellular localization of the wild-type exonuclease polypeptides are also contemplated by the invention. Mutant exonuclease polypeptides that result in dominant-negative phenotypes when introduced into a host cell are further contemplated. Presently preferred targets for the development of selective modulators include, for example: (i) regions of the exonuclease polypeptide that contact other proteins and/or localize the exonuclease polypeptide within a cell, (ii) regions of the exonuclease polypeptide that bind specific DNA sequences and (iii) conserved regions of the exonuclease polypeptides. Still other selective modulators include those that recognize specific exonuclease encoding and regulatory polynucleotide sequences.

The scientific value of the information contributed through the disclosures of DNA and amino acid sequences of the present invention is manifest. As one series of examples, knowledge of the sequence of cDNA encoding TREX1h, TREX2h, TREX1m, TREX2m, TREXDm or the conserved regions of the exonuclease makes possible through use of Southern hybridization or polymerase chain reaction (PCR) the identification of genomic DNA sequences encoding the polypeptide and expression control regulatory sequences such as promoters, operators, enhancers, repressors, and the like. DNA/DNA, DNA/RNA or RNA/RNA hybridization procedures carried out with DNA sequences of the invention under moderately to highly stringent conditions are likewise expected to allow the isolation of DNAs encoding allelic variants of exonucleases of the invention; allelic variants are known in the art to include structurally related proteins sharing one or more of the biochemical and/or immunological properties specific to, for example, TREX1h, TREX2h, TREX1m, TREX2m or TREXDm.

Similarly, non-human species genes encoding proteins homologous to exonucleases of the invention can also be identified by Southern and/or PCR analysis. As an alternative, complementation studies can be useful for identifying other human exonuclease products, as well as non-human proteins and DNAs encoding the proteins, that share one or more biological properties of an exonuclease of the invention. Of particular importance in this area would be the use of polynucleotides which encode the conserved regions or degenerate oligonucleotides designed to hybridize with the polynucleotides encoding the conserved regions as probes for identifying related proteins in human or non-human species. In identifying such exonucleases the creation of degenerate probes based on the conserved regions sequence will be invaluable. The creation of such probes will allow for the identification of other polynucleotides which encode similar polypeptides while maintaining a level of hybridization efficiency by taking advantage of the degeneracy the codons which regulate the amino acid sequence (i.e., several codons may code for the same amino acid).

Polynucleotides of the invention are also useful in hybridization assays to detect the capacity of cells to express exonucleases. Polynucleotides of the invention may also be the basis for diagnostic methods useful for identifying a genetic alteration(s) in an exonuclease locus that underlies a disease state or states.

Also made available by the invention are anti-sense polynucleotides that recognize and hybridize to polynucleotides encoding polypeptides of the invention. Full length and fragment anti-sense polynucleotides are provided. The worker of ordinary skill will appreciate that fragment anti-sense molecules of the invention include (i) those which specifically recognize and hybridize to exonuclease-encoding polynucleotides (as determined by sequence comparison of polynucleotides encoding an exonuclease of the invention to polynucleotides encoding other known molecules), (ii) those which recognize and hybridize to polynucleotides encoding other members of the exonuclease family of proteins, as well as (iii) those which recognize and hybridize to polynucleotides encoding the conserved regions. Antisense polynucleotides that hybridize to multiple polynucleotides encoding other members of the exonuclease family of proteins are also identifiable through sequence comparison to identify characteristic, or signature, sequences for the family of molecules. Anti-sense polynucleotides are particularly relevant to regulating expression of an exonuclease of the invention by those cells expressing exonuclease mRNA.

The antisense technology embraces gene therapy techniques to modulate exonuclease expression in vivo. Delivery sequences that modulate expression/activity of an exonuclease in target cells is effected in vivo or ex vivo by use of vectors, and more particularly viral vectors (e.g., adenovirus, adeno-associated virus, or a retrovirus), or ex vivo by use of physical DNA transfer methods (e.g., liposomes or chemical treatments). For reviews of gene therapy technology see Friedmann, Science, 244: 1275–1281 (1989); Verma, Scientific American: 68–84 (1990); and Miller, Nature, 357: 455–460 (1992). It is contemplated that in particular human disease states or therapeutic treatments, preventing the expression of, or inhibiting the activity of an exonuclease of the invention will be useful. Antisense nucleic acids (preferably 10 to 20 base pair oligonucleotides) capable of specifically binding to exonuclease expression control sequences or exonuclease RNA are introduced into cells (e.g., by a viral vector or colloidal dispersion system such as a liposome). Phosphothioate and methylphosphate antisense oligonucleotides are specifically contemplated for therapeutic use by the invention. The antisense oligonucleotides may be further modified by poly-L-lysine, transferrin polylysine, or cholesterol moieties at their 5' ends.

The invention further contemplates methods to modulate exonuclease expression through use of ribozymes. For a review, see Gibson and Shillitoe, Mol. Biotech. 7:125–137 (1997). Ribozyme technology can be utilized to inhibit translation of exonuclease mRNA in a sequence specific manner through (i) the hybridization of a complementary polynucleotide to a target mRNA and (ii) cleavage of the hybridized mRNA through nuclease activity inherent to the complementary strand. Ribozymes can be specifically designed or identified by empirical methods. Delivery of ribozymes to target cells can be accomplished using techniques well known and routinely practiced in the art, including for example, through use of targeting liposomes or viral vectors.

The invention further embraces methods to modulate transcription of an exonuclease of the invention through use of oligonucleotide-directed triplet helix formation. For a review, see Lavrovsky, et al., Biochem. Mot Med 62:11–22 (1997). Triplet helix formation is accomplished using sequence specific oligonucleotides that hybridize to double stranded DNA in the major groove as defined in the Watson-Crick model. Hybridization of a sequence-specific oligonucleotide can thereafter modulate activity of DNA-binding proteins, including, for example, transcription factors and polymerases. Preferred target sequences for hybridization include promoter and enhancer regions to permit transcriptional regulation of exonuclease expression.

Oligonucleotides that are capable of triplet helix formation are also useful for site-specific covalent modification of target DNA sequences. Oligonucleotides capable of modifying specific polynucleotide sequences are coupled to various DNA damaging agents as described in Lavrovsky, et al. [supra].

EXAMPLE 1

Determining Exonuclease Participation in DNA Incorporation of AraC

In view of the fact that many patients undergoing araC treatment are refractory to the drug or subsequently develop a drug resistance, it was proposed that, in these patients, araC may be incorporated into DNA at a decreased rate. One possibility is that the analog structure of araC may be recognized by proofreading exonuclease components of the polymerase which act to remove the analog and permit incorporation of dCTP.

HL-60 cells were incubated with 6-mercaptopurine (6-MP) to allow intracellular levels of thioinosine monophosphate (TIMP) to accumulate. TIMP has previously been shown to inhibit exonuclease activity specifically associated with DNA polymerase $\delta$ [Lee, et al. *Biochemistry* 19:215–219 (1980)]. Cytoplasmic 6-MP is converted to an active nucleotide metabolite TIMP by the action of hypoxanthine phosphoribosyltransferase (HPRT). Pharmacokinetic analysis of 6-MP metabolites indicated that pretreatment of HL-60 cells with 50 or 100 $\mu$M 6-MP resulted in accumulation of intracellular levels of TIMP -with peak concentration achieved at approximately twelve hours. Intracellular accumulation of TIMP was determined by HPLC [Zimm, et al., *Cancer Res.* 45:4156–4161 (1985)]. Upon addition of araC, the amount of araC incorporated into DNA increased and total DNA synthesis decreased in cells pretreated with 6-MP relative to untreated cells. At peak intracellular levels of TIMP, araC incorporation into DNA relative to total DNA synthesis was 20-fold greater in the 6-MP treated cells. The increased incorporation of araC into DNA resulted in an increase in cell killing as determined by growth curves and clonogenic assays of treated cells.

The increased incorporation of araC into the DNA was not the result of increased accumulation of araC in the 6-MP treated cells. Cells were treated with 6-MP for varying times for up to twelve hours followed by incubation with araCTP. At time points up to twelve hours, cells were treated with araC and harvested one hour after addition of araC. The nucleotides were then separated using HPLC, and intracellular araCTP was quantified. Results indicated that araCTP levels varied less than two-fold during the time course of the study, which was unlikely to account for the observed 20-fold increase in araC incorporation into DNA.

In order to assess the effect of intracellular TIMP that contributed to increased araC incorporation, exonuclease activity was partially purified from myeloblastic leukemia cells and in vitro enzyme inhibition studies ware carried out with TIMP. The majority of the cellular exonuclease activity was found in a band migrating on SDS-PAGE with a predicted molecular weight of 30 kDa.

Results indicated that TIMP inhibited the 30 kDa exonuclease with a $K_i$ of 17 $\mu$M, which strongly suggested that exonuclease inhibition occurred in vivo. Resistance to araC treatment by some AML cells may therefore arise as a result of exonuclease repair of araC-terminated DNA. Inhibition of the exonuclease activity in cells should, therefore, increase araC in DNA and increase cell killing. It is possible, however, that cell death may be attributable in part to 6-MP treatment alone.

Inhibition studies were also carried out with the purified 30 kD exonuclease and either TIMP or dGMP. The exonuclease was incubated in the presence of varying concentrations of dGMP or TIMP and results indicated TIMP was a more potent inhibitor that dGMP. The $K_i$ values for TIMP and dGMP were calculated to be 17 $\mu$M and 56 $\mu$M, respectively. Because the intracellular level of TIMP in murine leukemia cells treated for twelve hours with 6-MP has been shown to rise to approximately 180 $\mu$M, it is likely that the exonuclease activity is greatly abolished in those cells, thereby allowing the increase in araC incorporation into DNA.

Useful methods in the practice of this example include the following: DNA pol δ may be purified from human myeloblasts using the methods of Syvaoja et al. (Proc. Natl. Acad. Sci., USA 87:6664–6668, 1990) through step 5. The specific activity of the DNA pol δ preparation is preferably about 3,500 units/mg. A unit of DNA pol δ catalyzes the incorporation of 1 nmol of total nucleotide per hour at 37° C. using 100 $\mu$M poly(dAdT) as template and reaction conditions as described by Lewis et al. (Biochemistry 33:14620–14624, 1994). The 30 kDa exonuclease may be purified from human myeloblasts and from calf thymus using a modification of the published procedure (Perrino et al. J. Biol. Chem. 269:16357–16363, 1994). The CM-Sepharose column may be eliminated, and the ssDNA-cellulose column used prior to chromatography using a monoS FPLC column. The peak fractions from the monoS column are pooled, and ammonium sulfate added ($C_f$=25% saturation). The exonuclease sample is loaded onto a phenyl-Superose FPLC column previously equilibrated in buffer A (50 mM Tris, pH 8.2, 1 mM DTT, 1 mM EDTA, 10% glycerol) containing 25% ammonium sulfate. The column is washed with buffer A and eluted with a decreasing linear gradient of buffer A containing 25–0% ammonium sulfate into tubes containing α-lactalbumin ($C_f$=0.2 mg/ml). Dilutions of fractions are assayed for exonuclease activity, and the peak fractions are pooled, dialyzed against buffer A, and stored in aliquots at −80° C.

For primer extension, a 17 base oligonucleotide primer may be labeled with $^{32}$P at the 5' position and hybridized to a 35 mer DNA template at a 1:1 molar ratio (Perrino and Mekosh, J. Biol. Chem. 267:23043–23051, 1992. Reaction mixtures may be prepared containing 40 mM HEPES, pH 6.5, 1 mM MgCl$_2$, 10 mM KCl, 2 mM DTT, 0.03% Triton X-100, 2% glycerol, 80 $\mu$g/mL BSA, and 170 nM 17 mer-primed DNA template. For the 3'–5' exonuclease, a 20 mer or a 21 mer primer may be labeled with $^{32}$P and hybridized to the 35 mer DNA template. Reaction mixtures are prepared as described for the primer extension assays except a 10 nM template:primer and 0.0017 units of DNA pol δ. Reaction products are processed as described by Perrino and Loeb, (J. Biol. Chem:264, 2898–2905, 1989) and analyzed by electrophoresis through 15% polyacrylamide sequencing gels. Gels are fixed in 10% methanol/10% acetic acid, vacuum-dried, and exposed to Kodak XAR-5 film and quantified using an AMBIS radioanalytic imaging system.

To measure the 3'–5' exonuclease activity, a 23 mer is labeled with $^{32}$P at the 5' position and used in reactions as ssDNA. Reaction mixtures (10 $\mu$l) are prepared containing 20 mM Tris-HCl, pH 7.5, 10 mM MgCl$_2$, 2 mM DTT, 100 $\mu$g/mL BSA, 100 nM 23 mer, and 1 $\mu$l of the appropriate enzyme dilution. Incubation is 20 minutes at 37° C., and reactions are stopped by addition of 30 $\mu$l 95% ethanol. Samples are dried, resuspended in 5 $\mu$l 95% formamide, and analyzed by electrophoresis through 15% polyacrylamide sequencing gels. Radiolabeled bands are visualized and quantified by phosphorimagery (Molecular Dynamics). One unit of exonuclease is the amount of enzyme needed to degrade 1 pmol of 3' termini in 1 min at 37° C.

The phenyl-Superose purified exonuclease is incubated with AMP-resin (Sigma product # A-3019) in buffer B (20 mM Tris, 7.5, 2 mM DTT, 0.5 mM EDTA, 10% glycerol) containing 10 mM MgCl$_2$ for 30 minutes at 4° C. The resin is allowed to settle to the bottom of the tube, and unbound protein in the buffer above the resin is removed. The resin is washed three times with 0.5 ml of buffer B containing 10 mM MgCl$_2$, and bound proteins are eluted with sequential washes using 0.5 ml buffer B containing 0.5, 1.0, and 2.0 M NaCl and no MgCl$_2$. The collected samples are assayed for 3'–5' exonuclease activity.

The 3'–5' exonuclease activity may be detected in situ after SDS-PAGE using modified published procedures (Blank et al., Anal. Biochem. 120:267–275, 1982; Spanos and Hubscher, Methods in Enzymology. 91:263–727, 1983). Initially, the 30 kDa protein is identified after electrophoresis in a 12% SDS polyacrylamide gel containing a 3'$^{32}$P labeled DNA. To prepare the DNA 25 pmol of 20 mer is hybridized to 50 pmol of a KS+phagemid ssDNA (Stratagene), and the 20 mer is elongated with $^{32}$PαdATP using Klenow exo$^-$. The 3'$^{32}$P labeled DNA is added to the 12% acrylamide gel solution prior to casting the slab gel. After electrophoresis of samples, the SDS is extracted with 20 mM Tris, pH 7.5, 2 mM DTT, and the enzymes are renatured in 20 mM Tris, pH 7.5, 2 mM DTT, 0.4 mg/ml BSA, and 10% glycerol. To assay for 3'–5' exonuclease, MgCl$_2$($C_f$=10 mM) is added, and the gel is incubated at 37° C. The gel is dried and exposed to film.

To detect the products of the 3'–5' exonuclease in situ a modified published procedure may used (Longley and Mosbaugh, Biochemistry 30:2655–266423, 1991). In this gel assay a 5'$^{32}$P-labeled 20 mer is hybridized to the phagemid template. After electrophoresis, the SDS is extracted, proteins are renatured in situ, and the gel lanes are sliced vertically. Gel slices are incubated at 37° C. for 1 hr in exonuclease reaction buffer, and the gel slices are polymerized horizontally on top of a 15% urea-polyacrylamide DNA sequencing gel. After electrophoresis the sequencing gel is dried and exposed to film.

Logarithmically growing cultures of HL-60 cells are incubated with 6-MP for varying times. The cultures are divided into two groups. The first group is treated with 1 $\mu$M $^3$H-araC for 1 hour to measure araC in DNA. The second group is treated with $^3$H-thymidine and 1 $\mu$M unlabeled araC for 1 hour to measure total DNA synthesis. Cells are pelleted, washed with PBS, and $^3$H-araC or $^3$H-thymidine in acid insoluble material is determined by scintillation counting. To measure araCTP in HL-60 cells, 6-MP treated samples are incubated with 1 $\mu$M $^3$H-araC. Cells are pelleted and washed with PBS. The acid soluble nucleotides are collected and separated by HPLC (Partisil 10 SAX, Whatman). The fraction containing $^3$HaraCTP is quantified by scintillation counting.

EXAMPLE 2

Isolation of Human Myeloblastic Leukemia and Bovine Thymus Exonucleases

In order to identify the 30 kDa protein exhibiting the predominant exonuclease activity in human myeloblastic leukemia and bovine thymus cells, protein purification was carried out essentially as described in Perrino, et al., *J Biol. Chem.* 269:16357–16363 (1994). For protein purification from bovine thymus, an additional step using phenyl SUPEROSE was employed.

In order to detect exonuclease activity in the cell extract, a biochemical assay was developed using DNA polymerase a and an oligonucleotide template primer with an araC analog at the 3' terminus. In this assay, incorporation of radiolabeled nucleotides into the araC-template primer by the polymerase first requires that the araC analog be removed by a 3'–5' exonuclease.

A 30 kDa enzyme was found in both cell types that possessed 3'–5' exonuclease activity. The 3'–5' exonuclease activity suggests that this enzyme plays a role in DNA repair. The apparent rate of araC removal by the exonuclease was approximately the same rate as the rate of deoxynucleotide monophosphate removal. Furthermore, the apparent rate of 3' terminal excision was approximately the same whether the template primer was hybridized to a complementary strand or not, indicating that the enzyme possessed both single and double stranded 3'–5' exonuclease activity. No 5'–3' exonuclease was detected, nor was the exonuclease activity found to be associated with polymerase activity.

The AML exonuclease and other previously identified enzymes share similar characteristics, but significant differences distinguish the AML activity. For example, the 30 kD AML enzyme resembles DNaseIII and DNaseVII in that all three degrade single or double stranded DNA in a 3'–5' direction only and require a divalent cation for activity. Substrate specificity indicates, however, that the AML enzyme is distinct in that it does not degrade 3'-phosphoryl-terminated DNA like DNaseIII and DNaseVII. In addition, the products of DNaseIII digestion are both 5' mononucleotides and dinucleotides, while the products of AML exonuclease and DNaseVII activity are exclusively 5' mononucleotides.

EXAMPLE 3

Cloning of the Human TREX1h Gene

In order to identify a cDNA encoding the TREX1h polypeptide, the following procedure was carried out. The purified bovine exonuclease was digested with trypsin and resulting proteolytic fragments were separated by HPLC. The amino acid sequences of four internal peptides (SEQ ID NOs: 5, 6, 7, and 8) were determined by Edman degradation and provided 53 amino acids of the primary sequence of the enzyme.

Ala-Phe-Asp-Ala-Asp-Leu-Asn-Leu-Ile-Arg SEQ ID NO:5

Tyr-Ala-Leu-Glu-Leu-Ser-Ala-Pro-Gln-Gly-Pro-Ser-Pro-Thr-Ala-Pro-Val SEQ ID NO:6

Ala-Leu-Glu-Pro-Thr-Gly-Ser-Ser-Ser-Glu-His-Gly-Pro-Arg SEQ ID NO:7

Xaa-Tyr-Asp-Leu-Gly-Xaa-Val-Tyr-Xaa SEQ ID NO:8

Degenerate oligonucleotides were prepared based on the amino acid sequence of two of the four peptides and used in polymerase chain reaction (PCR) as described below. The primer sequences are:

TAGCATGAATTCTA(T/C)GCN(T/C)TNGA(A/G)GG SEQ ID NO:9

GCATCAGGATCCTCNGC(G/A)TC(G/A)AANGC SEQ ID NO:10

TCAGCAGAATTCGCI(T/C)TIGA(A/G)GGI(T/C)TI(T/A)(G/C)IGCICCICA(A/G)GG SEQ ID NO:11

GGTGTTGGATCCIC(T/G)IATIA(A/G)(A/G)TTIAGIA(A/G)(A/G)TCIGC(G/A)TC SEQ ID NO:12

PCR was carried out as follows: The 100 μl reaction included 10 mM Tris-HCl, pH 9.0, 0.1% Triton X-100, 2.5 mM MgCl$_2$, 0.5 mM dNTPs, 5 μg bovine cDNA, 1 μM each primer, and 2.5 units Taq polymerase. Amplification was carried out with five cycles of 95° C. for one minute, 37° C. for one minute, a two minute ramp to 74° C. for one minute, and then thirty cycles of 95° C. for one minute, 55° C. for one minute, and 74° C. for one minute. The bovine cDNA was prepared from total RNA isolated from thymus tissue using cesium chloride equilibrium density centrifugation. mRNA was isolated from total RNA using an oligo(dT) column, and cDNA was prepared using a synthesis kit (Gibco/BRL) according to manufacturer's suggested protocol.

PCR resulted in amplification of a 201 base pair fragment, which was cloned and sequenced. Sequence analysis indicated that the PCR product encoded twelve amino acids in the two peptides from which the PCR primers were designed, thereby providing the primary amino acid sequence for a contiguous 67 amino acid fragment of the bovine exonuclease.

The DNA and protein sequences of the bovine enzyme were used as query sequences in the Expressed Sequence Tag (EST) database available through Genbank. Two human cDNA clones, #704410 (identified by 5' EST AA279657, SEQ ID NO:13, and 3' EST AA279658, SEQ ID NO:14) and #131083 (identified by 5' EST R23917, SEQ ID NO:15, and 3' EST R23918, SEQ ID NO:16) were identified in the database. These sequences did not include complete open reading frames as evidenced by the lack, in both, of an initiating methionine codon. The sequences for the two human clones were then used as query sequences to search the EST database a second time and a mouse clone, #671838 (identified by 5' EST AA242227, SEQ ID NO:17, and a second clone, identified by 5' EST AA896411, SEQ ID NO:18) encoding a complete open reading frame was identified. Finally, the database was searched a third time using the mouse clone and a third human clone, #306966 (identified by 3' EST N91973, SEQ ID NO:19, and 5' EST W24304, SEQ ID NO:20) was identified, and which included a complete open reading frame.

The resulting open reading frame encoded a 304 amino acid protein that was designated TREX1h. The inventor made the surprising discovery, however, that the sequence cloned as described was incomplete, or was an alternately spliced variant of the TREX1h gene. A primer was constructed to hybridize near the 5' end of the cDNA and was matched with a primer constructed to hybridize within the gene coding sequence for a polymerase chain reaction using a human genomic sequence as the target. Surprisingly, a gene was isolated that encoded a 314 amino acid protein and that included ten amino acids at the N-terminus of the sequence isolated from the cDNA target. This newly discovered human genomic sequence has been designated by the inventor as TREX1h, and the nucleotide sequence is set out in SEQ ID NO:1. The amino acid sequence of the polypeptide is set out in SEQ ID NO:2. Analysis of the amino acid sequence for TREX1h indicated sequence identity within the predicted exonuclease domain.

The genomic TREX1h gene sequence is as follows with the coding sequence underlined:

```
  1 CAGGGGCTCCCAGCAGTGTGTAAGACCGGGAGCTGGTCTGGCACCACTGC (SEQ ID NO:1)

51 CCTGGTCCTTCCAGCTGCCTGTCACTGGTATGATGGCCCCGGTGCATTGT

101 GCCACCAGCAGGCCACAGCTGTGGATCTTGGAAGGCCTCTGGGGTCCCCC

151 GGGAGCAGGGGAGTGGGTGTGGGGGGAACGGATGGTGGTGAGAGGGACA

201 GACCAGGCAGGCTGACGAGCAGGGCGGGCCTGGCTCACGTGGGCCTGTAG

251 GCGGGCCCACGCCAAGTTTCACTTCCCGCCACTGCTGCCAGCGAGAGCCG

301 CGGGAGAGTGTGCAGCCGAGTCACTACTGCCTGCCTGCCTGCCTGCTACG

Donor site 1
351 GTGAGTGTGGCCCCCACAATGGGATGGCGCAGGGCAGGAGGGCCATGGGT

401 TCCCCCACCCCAGACTAAGGGGGCACTAGGGGAGGGGCCGAGTCATGTGA

451 AGAGGGAGACCCTCTCAGACAGTCGAATGTGCTGGTCCCACTAAGGAAAC

501 CACCTCACCCTCTCCAACTTCCTGCCTGAAAATGGGCCTGGAGCTCGCA

551 GACAGGGCAGGATTGTGCAGGGAAGGCCTGAGATGTGCTTCTGCCCACCC

601 CCTACCCCACTCCCTCCCCTTCGGATCTTAACACTGGGCACTCACACACC predicted acceptor site  New Start site
651 CACCCCATGCTCCTCTACCAGGCTCAGCAGCAGGTACGTACCCAACCATG 10   Old Start site
701 GGCTCGCAGGCCCTGCCCCCGGGGCCCATGCAGACCCTCATCTTTTTCGA Acceptor site 1
751 CATGGAGGCCACTGGCTTGCCCTTCTCCCAGCCCAAGGTCACGGAGCTGT

801 GCCTGCTGGCTGTCCACAGATGTGCCCTGGAGAGCCCCCCACCTCTCAG

851 GGGCCACCTCCCACAGTTCCTCCACCACCGCGTGTGGTAGACAAGCTCTC

901 CCTGTGTGTGGCTCCGGGGAAGGCCTGCAGCCCTGCAGCCAGCGAGATCA

951 CAGGTCTGAGCACAGCTGTGCTGGCAGCGCATGGGCGTCAATGTTTTGAT

1001 GACAACCTGGCCAACCTGCTCCTAGCCTTCCTGCGGCGCCAGCCACAGCC

1051 CTGGTGCCTGGTGGCACACAATGGTGACCGCTACGACTTCCCCCTGCTCC

1101 AAGCAGAGCTGGCTATGCTGGGCCTCACCAGTGCTCTGGATGGTGCCTTC

1151 TGTGTGGATAGCATCACTGCGCTGAAGGCCCTGGAGCGAGCAAGCAGCCC

1201 CTCAGAACACGGCCCAAGGAAGAGCTACAGCCTAGGCAGCATCTACACTC

1251 GCCTGTATGGGCAGTCCCCTCCAGACTCGCACACGGCTGAGGGTGATGTC

1301 CTGGCCCTGCTCAGCATCTGTCAGTGGAGACCACAGGCCCTGCTGCGGTG

1351 GGTGGATGCTCACGCCAGGCCTTTCGGCACCATCAGGCCCATGTATGGGG

1401 TCACAGCCTCTGCTAGGACCAAGCCAAGACCATCTGCTGTCACAACCACT

1451 GCACACCTGGCCACAACCAGGAACACTAGTCCCAGCCTTCGAGAGAGCAG

1501 GGGTACCAAGGATCTTCCTCCAGTGAAGGACCCTGGAGCCCTATCCAGGG

1551 AGGGGCTGCTGGCCCCACTGGGTCTGCTGGCCATCCTGACCTTGGCAGTA

1601 GCCACACTGTATGGACTATCCCTGGCCACACCTGGGGAGTAGGCCAAGAA

1651 GGAAAATCTGACGAATAAAGACCCCCGCTGCCCCATA
```

Possible promoter sequences that appear in this gene include a sequence at bases 9–59 (with transcription start at 49) and bases 519–569 (with transcription start at 559). It is understood that primers hybridizing to any portion of this sequence may be used in a pair with random primers such as random hexamers or random pentamers to isolate further control sequences upstream of this sequence in the genome.

EXAMPLE 4

Expression of TREX1h

The EST encoding human TREX1h was obtained from Genome Systems (St Louis, Mo.) and sequenced. The complete open reading frame was subcloned into parental vector pCMV5B as follows:

Two oligomer primers were synthesized (SEQ ID NOs: 21 and 22) for use in PCR to amplify the coding region of the TREX1h EST:

ACTCATACGTCGACAGGAGG-
TAAAAAAAAATGCAGACCCTCATCT SEQ ID NO:21

GTAAAACGACGGCCAGT SEQ ID NO:22

The 5' primer (SEQ ID NO:21) included an XhoI restriction site, a ribosome binding site, and 16 nucleotides complementary to the 5' end of the TREX1h gene. The 3' primer (SEQ ID NO:22) included 17 nucleotides complementary to the plasmid vector. PCR was performed under the following conditions: 95° C. for 30 seconds, 60° C. for 30 seconds, and 72° C. for on The amplification product was digested with Ahol and HindIII and ligated into vector pOXO4 [Parsonage, et al. *J. Biol. Chem.* 268:3161–3167 (1993)] previously digested with the same enzymes to give an expression plasmid designated as pTREX1h/T7.

The pTREX1h/T7 plasmid was electroporated into BL21/DE3 cells, which were grown at 23° C. to a density of $OD_{595}$ 0.3. Isopropylthiogalactopyranoside (IPTG) was added to induce overexpression and incubation of the cells was continued overnight. Protein extracts were prepared from the cells and enzyme activity assayed using a $^{32}P$-labeled 23 nucleotide oligomer.

Results indicated that the exonuclease activity in cells transfected with TREX1h coding sequences was 30 fold higher than in control cells transfected only with the parental vector, which indicated that the EST encoded an exonuclease.

EXAMPLE 5

Identification of Polynucleotide Encoding Additional TREX1h-Like Polypeptides Having determined the cDNA encoding human TREX1h, the full length sequence was used as the query sequence in a subsequent search of the available databases.

TREX2h and TREX2m

A COSMID (Genbank #AF002998) comprising a 45 kb human genomic sequence in which a region related to that encoding TREX1h was identified by searching the Genbank database using the cDNA for TREX1h as query. The region with homology to the TREX1h-encoding sequence was designated TREX2h. Interestingly, the TREX2h genomic sequence did not include any intron sequences. The polynucleotide and amino acid sequences for TREX2h are set out in SEQ ID NO:3 and 4, respectively. Sequence analysis of the TREX2h open reading frame indicated greater than 55% identity with the polynucleotide encoding TREX1h.

The open reading frame identified in AF002998 and related to TREX1h was then used to search the EST database. Results of the search indicated that no human EST contained the sequence. The apparent lack of an EST corresponding to this sequence raises questions about the level of expression of this gene in human cells. The search did identify, however, a mouse sequence, #480859 (identified by 5' EST AA060540, SEQ ID NO:23) which was designated TREX1m, and a second clone, #804515, (identified by 5' EST AA474437, SEQ ID NO:24), which encoded a complete open reading frame that was designated as TREX2m.

The genomic sequence identified above permits design and synthesis of PCR primers that are used to amplify the human sequence from readily available genomic sources. The primer pair set out in SEQ ID NO:25 and SEQ ID NO:26 is used in amplification reactions as described above for TREX1h.

GCGTCAAGCTTGGGAACATCACCATGTC-
CGAGGCACCCCGG SEQ ID NO:25

GTCGCGGATCCTGGCCCTGGTGCTCAG-
GCCTCCAGGCTGGG SEQ ID NO:26

The resulting amplification product is inserted into an expression vector and introduced into host cells as described above or by use of any of the number of techniques well known and routinely practiced in the art.

The mouse TREX2m sequence was subcloned as described above for TREX1h using the 5' primer set out in SEQ ID NO:27 and the 3' primer used to amplify TREX1h (SEQ ID NO:22).

AGTGATACAGTCGACAGGAGG-
TAAAAAAAAATGTCTGAGCCACCCCG SEQ ID NO:27

Template DNA was the mouse EST 480859. PCR was carried out as described for TREX1h and the resulting amplification product was subcloned as for TREX1h. The resulting expression plasmid was designated pTREX2m/T7 and expression of the encoded gene was carried out as described for TREX1h. Protein extract from the electroporated cells included 30 fold greater exonuclease activity than protein from control cells having only the parental vector.

TREX3h

A polynucleotide encoding a third exonuclease species designated TREX3h was also identified in a human EST during database searches. The coding region for TREX3h was found to exhibit approximately 41% identity to the open reading frame for TREX1h and approximately 39% identity with the coding region for TREX2h. An EST encoding a portion of the TREX1h gene has previously been reported to encode an exonuclease [Koonin, *Crr. Biol.* 7:R604–R606 (1997)]. The coding region for the protein is amplified by PCR using the 5' primer below in combination with the 3' primer used to amplify TREX1h (SEQ ID NO:22).

ACTCATACGTCGACAGGAGG-
TAAAAAAAAATGGTCTCAGCGGATG SEQ ID NO:28

Amplification is carried out as described above and the PCR product is subcloned as described to give plasmid pTREX3h/T7. Bacterial expression is carried out as for expression of TREX1h and TREX2m, above.

An exonuclease family sequence has also been identified from a library of *Drosophila melanogaster* sequences. The *D. melanogaster* nucleotide sequence is disclosed herein as SEQ ID NO:33 and the derived amino acid sequence is identified herein as SEQ ID NO:34.

EXAMPLE 6

Expression in Mammalian Cells

The TREX1h, TREX2m, and TREX3h encoding sequences are digested from the bacterial expression plasmids described above using Xhol and HindIII and cloned into the mammalian expression vector pCMV5b previously digested with the same enzymes. The resulting expression constructs are designated pTREX1h/CMV, pTREX2m/CMV and pTREX3h/CMV. The individual plasmids are transfected into COS cells, which are grown for two days following transfection. Protein extracts are prepared and exonuclease activity is measured using the $^{32}P$-labeled 23 nucleotide oligomer as described above.

In a second method of expression in a mammalian cell, the TREX1h and TREX2h genes have been cloned into mammalian expression vectors in the forward and reverse directions to generate stable cell lines that over and under-express the TREX1h gene products. The TREX1h and TREX2h sequences were cloned into the pTRE plasmid (Clontech) for expression, and the TREX1h gene was cloned into this plasmid in the reverse orientation to express the TREX1h antisense mRNA. In a preliminary step, cell lines were generated from HeLa and HL-60 cells that contain the stably integrated pTET-OFF plasmid (Clontech). These cells incorporate the Clontech Tet-off system establishing cell lines that express the tetRVP 16 fusion protein. The tetR protein binds at the tetO operator in the absence of tetracycline. The tetR protein has been fused to the C-terminal 127 amino acids of the mammalian cell transcription activator protein VP16 (Herpes Simplex Virus). Thus, in the absence of tetracycline the tetRVP16 protein binds the TRE and induces transcription of downstream genes, while in the presence of tetracycline the tetRVP16 protein does not associate with the TRE. The pTET-OFF plasmid also contains a neomycin resistance gene to allow the selection of stable clones with G418. Colonies were picked, transiently transfected with the pTRE-LUC plasmid (Clontech) and tested for induction levels. The pTRE-LUC plasmid contains the luciferase gene downstream of the Tet Responsive elements in the pTRE plasmid. Cells with low background and high induction levels of expression were chosen for transfection with the TREX1h and TREX2h genes. The TREX1h and TREX1m genes were then cloned into the pTRE plasmid downstream from the TRE (Tet responsive element). The TREX containing plasmids, as well as the empty pTRE vector, were cotransfected with the pTK-HYG plasmid (Clontech) into the HeLa and HL-60 tetRVP16 expressing cell lines. Stable cell lines were selected using the hygromycin resistance marker located on the pTK-HYG plasmid. Cell lines with varying expression levels of the TREX1h and TREX2h genes were selected for subsequent studies. Expression levels were measured using exonuclease assays and RT-PCR.

The Ecdysone System (Invitrogen) uses the steroid hormone ecdysone analog, ponasterone A, to activate the TREX genes by way of a heterodimeric nuclear receptor. A cell line is generated that has stably integrated the pVgRXR plasmid (Invitrogen) containing the RXR (retinoid X receptor) and VgEcR receptor (a modified form of the ecdysone receptor to which the VP16 transactivation domain has been fused). These two products form a heterodimer that binds to the ecdysone response element (ERE) in the presence of the synthetic analog ponasterone A. Cells (HeLa and HL-60) were transfected with the pVgRXR plasmid and stable clones were selected using the zeocin resistance marker located on the pVgRXR plasmid. Colonies were picked, transiently transfected with the pIND-GFP plasmid (Invitrogen) and tested for induction levels. The pIND-GFP plasmid contains the green fluorescence protein (GFP) gene downstream of the Tet Responsive elements in the pTRE plasmid. Cell lines shown to have low background and high induction levels of expression were then transfected with the pIND plasmid (Invitrogen) empty vector as well as pIND vectors containing the TREX1h or TREX2h genes located downstream of the ecdysone response element. Stable clones were selected using the neomycin resistance marker located in the pIND vector. Cell lines with varying expression levels of the TREX genes were selected for subsequent studies. Expression levels were measured using exonuclease assays and RT-PCR.

EXAMPLE 7

Screening Candidate Substances as Effectors of Exonuclease Activity

The TREX1h and TREX2h proteins have been cloned into prokaryotic expression vectors and expressed in bacteria. The proteins have been purified using standard chromatography procedures. A screening assay has been designed to identify compounds that inhibit the exonuclease activity of the TREX exonucleases. A radiolabeled or fluorescently labeled DNA oligomer is incubated with the purified recombinant enzyme in the absence or presence of the test compound. Activity of the enzyme is detected by examination of the length of the oligomer products by DNA sequencing gel analysis or by loss of the fluorescently labeled nucleotide from the oligomer. Compounds that demonstrate inhibitory activity toward the TREX exonucleases are tested for chemotherapeutic potential.

The TREX1h expressing cells are used to identify specific drugs that increase the chemosensitivity of cells to a variety of chemotherapeutic nucleotide analogs. Cell lines containing the mammalian expression plasmids, with and without the TREX genes, are incubated with a currently available nucleoside analog. Cells lines expressing the TREX genes are expected to survive higher drug concentrations than nonexpressing cell lines. A screening assay has been designed to identify compounds that increase the sensitivity of the TREX expressing cell lines to the first drug. Cells that are not expressing the TREX proteins are not expected to be sensitive to this TREX-specific compound. A 96 well plate contains TREX-expressing cells contacted with the drug and cytotoxicity is measured by rhodamine assay. Cytotoxicity is then measured for cells contacted with the drug (X) plus a candidate substance, compound (Y). Compounds (Y) that increase cytotoxicity for TREX expressing cells are tested for chemotherapeutic potential.

While the present invention has been described in terms of specific embodiments, it is understood that variations and modifications will occur to those skilled in the art. Accordingly, only such limitations as appear in the appended claims should be placed on the invention.

What is claimed is:

1. A composition comprising an isolated nucleic acid molecule, wherein said nucleic acid molecule or its full length complement encodes the amino acid sequence of SEQ ID NO:2.

2. A composition comprising an isolated nucleic acid molecule, wherein the nucleic acid molecule comprises the nucleic acid sequence of SEQ ID NO:1 or its full length complement.

3. The composition of claim 2, wherein the nucleic acid molecule comprises bases 697–1638 of SEQ ID NO:1 or the full length complement thereof.

4. The composition of claim 1 wherein the nucleic acid molecule or its complement hybridizes to a nucleic acid segment having the sequence of SEQ ID NO:1 under conditions including hybridization at 50° C. in 1×SSC, and washing at 65° C. in 0.1×SSC.

5. The composition of claim 1, wherein said polypeptide encoding region is operatively linked to a promoter.

6. The composition of claim 1, wherein said polypeptide encoding region is operatively linked to a heterologous promoter.

7. The composition of claim 1, wherein said polypeptide encoding region is linked to a marker gene.

8. The composition of claim 1, wherein said polypeptide encoding region is contained in a vector.

9. The composition of claim 8, wherein said vector is an expression vector.

10. The composition of claim 8, wherein said vector is a viral vector.

11. The composition of claim 8, wherein said vector is a plasmid.

12. A host cell that contains the nucleic acid composition of claim 8.

13. A host cell of claim 12, wherein said host cell is a bacterial cell.

14. A host cell of claim 12, wherein said host cell is a mammalian cell.

* * * * *

UNITED STATES PATENT AND TRADEMARK OFFICE
CERTIFICATE OF CORRECTION

PATENT NO. : 6,632,665 B1
DATED : October 14, 2003
INVENTOR(S) : Perrino

It is certified that error appears in the above-identified patent and that said Letters Patent is hereby corrected as shown below:

Title page,
Item [56], References Cited, OTHER PUBLICATIONS, please replace "Joines" with -- Joins --; please replace "Exonuclease," with -- Exonucleases --; please replace "1-B-D" with -- 1-ß-D --; please replace "Cloning of" with -- Cloning and --; please replace "3'-5'-Exanuclease" with -- 3'-5'-Exonuclease --; and please replace "untill" with -- until --.

Column 23,
Lines 7-8, please replace "polymcrasc a and an" with -- polymcrasc and an --;

Column 28,
Line 31, please replace "TRLX1h" with -- TREX3L --.

Signed and Sealed this

Twentieth Day of April, 2004

JON W. DUDAS
*Acting Director of the United States Patent and Trademark Office*

SEQUENCE LISTING

<160> NUMBER OF SEQ ID NOS: 34

<210> SEQ ID NO 1
<211> LENGTH: 1686
<212> TYPE: DNA
<213> ORGANISM: HOMO SAPIENS
<220> FEATURE:
<221> NAME/KEY: CDS

<222> LOCATION: (697)..(1638)

<400> SEQUENCE: 1

```
caggggctcc cagcagtgtg taagaccggg agctggtctg gcaccactgc cctggtcctt      60
ccagctgcct gtcactggta tgatggcccc ggtgcattgt gccaccagca ggccacagct     120
gtggatcttg gaaggcctct gggtccccc gggagcaggg gagtgggtgt gggggggaac     180
ggatggtggt gagagggaca gaccaggcag gctgacgagc agggcgggcc tggctcacgt     240
gggcctgtag gcgggcccac gccaagtttc acttaccgcc actgctgcca gcagagagccg     300 cgggagagtg tgcagccgag tcactactgc ctgcctgcct gcctgctacg gtgagtgtgg     360
cccccacaat gggatggcgc agggcaggag ggccatgggt tccccacc cagactaagg     420 gggcactagg ggaggggccg agtcatgtga agagggagac cctctcagac agtcgaatgt     480
gctggtccca ctaaggaaac cacctcaccc tctccaactt cctgcctgaa atgggcccct     540
ggagctcgca gacagggcag gattgtgcag ggaaggcctg agatgtgctt ctgcccaccc     600
cctaccccac tccctcccct tcggatctta acactgggca ctcacacacc cacccatgc     660 tcctctccag gctcagcagc aggtacgtac ccaacc atg ggc tcg cag gcc ctg        714
                                         Met Gly Ser Gln Ala Leu
                                          1               5 ccc ccg ggg ccc atg cag acc ctc atc ttt ttc gac atg gag gcc act       762
Pro Pro Gly Pro Met Gln Thr Leu Ile Phe Phe Asp Met Glu Ala Thr
            10                  15                  20 ggc ttg ccc ttc tcc cag ccc aag gtc acg gag ctg tgc ctg ctg gct       810
Gly Leu Pro Phe Ser Gln Pro Lys Val Thr Glu Leu Cys Leu Leu Ala
        25                  30                  35 gtc cac aga tgt gcc ctg gag agc ccc ccc acc tct cag ggg cca cct       858
Val His Arg Cys Ala Leu Glu Ser Pro Pro Thr Ser Gln Gly Pro Pro
    40                  45                  50 ccc aca gtt cct cca cca ccg cgt gtg gta gac aag ctc tcc ctg tgt       906
Pro Thr Val Pro Pro Pro Pro Arg Val Val Asp Lys Leu Ser Leu Cys
55                  60                  65                  70 gtg gct ccg ggg aag gcc tgc agc cct gca gcc agc gag atc aca ggt       954
Val Ala Pro Gly Lys Ala Cys Ser Pro Ala Ala Ser Glu Ile Thr Gly
                75                  80                  85 ctg agc aca gct gtg ctg gca gcg cat ggg cgt caa tgt ttt gat gac      1002
Leu Ser Thr Ala Val Leu Ala Ala His Gly Arg Gln Cys Phe Asp Asp
            90                  95                 100 aac ctg gcc aac ctg ctc cta gcc ttc ctg cgg cgc cag cca cag ccc      1050
Asn Leu Ala Asn Leu Leu Leu Ala Phe Leu Arg Arg Gln Pro Gln Pro
        105                 110                 115 tgg tgc ctg gtg gca cac aat ggt gac cgc tac gac ttc ccc ctg ctc      1098
Trp Cys Leu Val Ala His Asn Gly Asp Arg Tyr Asp Phe Pro Leu Leu
    120                 125                 130 caa gca gag ctg gct atg ctg ggc ctc acc agt gct ctg gat ggt gcc      1146
Gln Ala Glu Leu Ala Met Leu Gly Leu Thr Ser Ala Leu Asp Gly Ala
135                 140                 145                 150 ttc tgt gtg gat agc atc act gcg ctg aag gcc ctg gag cga gca agc      1194
Phe Cys Val Asp Ser Ile Thr Ala Leu Lys Ala Leu Glu Arg Ala Ser
                155                 160                 165 agc ccc tca gaa cac ggc cca agg aag agc tac agc cta ggc agc atc      1242
Ser Pro Ser Glu His Gly Pro Arg Lys Ser Tyr Ser Leu Gly Ser Ile
            170                 175                 180 tac act cgc ctg tat ggg cag tcc cct cca gac tcg cac acg gct gag      1290
Tyr Thr Arg Leu Tyr Gly Gln Ser Pro Pro Asp Ser His Thr Ala Glu
        185                 190                 195 ggt gat gtc ctg gcc ctg ctc agc atc tgt cag tgg aga cca cag gcc      1338
```

```
Gly Asp Val Leu Ala Leu Leu Ser Ile Cys Gln Trp Arg Pro Gln Ala
        200                 205                 210 ctg ctg cgg tgg gtg gat gct cac gcc agg cct ttc ggc acc atc agg    1386
Leu Leu Arg Trp Val Asp Ala His Ala Arg Pro Phe Gly Thr Ile Arg
215                 220                 225                 230 ccc atg tat ggg gtc aca gcc tct gct agg acc aag cca aga cca tct    1434
Pro Met Tyr Gly Val Thr Ala Ser Ala Arg Thr Lys Pro Arg Pro Ser
                235                 240                 245 gct gtc aca acc act gca cac ctg gcc aca acc agg aac act agt ccc    1482
Ala Val Thr Thr Thr Ala His Leu Ala Thr Thr Arg Asn Thr Ser Pro
            250                 255                 260 agc ctt gga gag agc agg ggt acc aag gat ctt cct cca gtg aag gac    1530
Ser Leu Gly Glu Ser Arg Gly Thr Lys Asp Leu Pro Pro Val Lys Asp
        265                 270                 275 cct gga gcc cta tcc agg gag ggg ctg ctg gcc cca ctg ggt ctg ctg    1578
Pro Gly Ala Leu Ser Arg Glu Gly Leu Leu Ala Pro Leu Gly Leu Leu
280                 285                 290 gcc atc ctg acc ttg gca gta gcc aca ctg tat gga cta tcc ctg gcc    1626
Ala Ile Leu Thr Leu Ala Val Ala Thr Leu Tyr Gly Leu Ser Leu Ala
295                 300                 305                 310 aca cct ggg gag taggccaaga aggaaaatct gacgaataaa gaccccgct          1678
Thr Pro Gly Glu gccccata                                                            1686

<210> SEQ ID NO 2
<211> LENGTH: 314
<212> TYPE: PRT
<213> ORGANISM: HOMO SAPIENS

<400> SEQUENCE: 2

Met Gly Ser Gln Ala Leu Pro Pro Gly Pro Met Gln Thr Leu Ile Phe
  1               5                  10                  15

Phe Asp Met Glu Ala Thr Gly Leu Pro Phe Ser Gln Pro Lys Val Thr
                 20                  25                  30

Glu Leu Cys Leu Leu Ala Val His Arg Cys Ala Leu Glu Ser Pro Pro
             35                  40                  45

Thr Ser Gln Gly Pro Pro Pro Thr Val Pro Pro Pro Arg Val Val
         50                  55                  60

Asp Lys Leu Ser Leu Cys Val Ala Pro Gly Lys Ala Cys Ser Pro Ala
 65                  70                  75                  80

Ala Ser Glu Ile Thr Gly Leu Ser Thr Ala Val Leu Ala Ala His Gly
                 85                  90                  95

Arg Gln Cys Phe Asp Asp Asn Leu Ala Asn Leu Leu Leu Ala Phe Leu
            100                 105                 110

Arg Arg Gln Pro Gln Pro Trp Cys Leu Val Ala His Asn Gly Asp Arg
        115                 120                 125

Tyr Asp Phe Pro Leu Leu Gln Ala Glu Leu Ala Met Leu Gly Leu Thr
    130                 135                 140

Ser Ala Leu Asp Gly Ala Phe Cys Val Asp Ser Ile Thr Ala Leu Lys
145                 150                 155                 160

Ala Leu Glu Arg Ala Ser Ser Pro Ser Glu His Gly Pro Arg Lys Ser
                165                 170                 175

Tyr Ser Leu Gly Ser Ile Tyr Thr Arg Leu Tyr Gly Gln Ser Pro Pro
            180                 185                 190

Asp Ser His Thr Ala Glu Gly Asp Val Leu Ala Leu Leu Ser Ile Cys
        195                 200                 205
```

```
Gln Trp Arg Pro Gln Ala Leu Leu Arg Trp Val Asp Ala His Ala Arg
    210                 215                 220

Pro Phe Gly Thr Ile Arg Pro Met Tyr Gly Val Thr Ala Ser Ala Arg
225                 230                 235                 240

Thr Lys Pro Arg Pro Ser Ala Val Thr Thr Ala His Leu Ala Thr
                245                 250                 255

Thr Arg Asn Thr Ser Pro Ser Leu Gly Glu Ser Arg Gly Thr Lys Asp
            260                 265                 270

Leu Pro Pro Val Lys Asp Pro Gly Ala Leu Ser Arg Glu Gly Leu Leu
        275                 280                 285

Ala Pro Leu Gly Leu Leu Ala Ile Leu Thr Leu Ala Val Ala Thr Leu
290                 295                 300

Tyr Gly Leu Ser Leu Ala Thr Pro Gly Glu
305                 310

<210> SEQ ID NO 3
<211> LENGTH: 1717
<212> TYPE: DNA
<213> ORGANISM: HOMO SAPIENS
<220> FEATURE:
<221> NAME/KEY: CDS
<222> LOCATION: (755)..(1462)

<400> SEQUENCE: 3
```

| | | | |
|---|---|---|---|
| gagctagcga gggggtggcg agcgagccgg ctgcgcaggt cctgaggccc caggcctcat | | | 60 |
| tgttggccaa caggcagctg ggggcgggct gcggccgctg attaaaggcc gcctagagca | | | 120 |
| gcctgtgtgg cgacaggtgc ccagaagccc aggaagccgg tcagtgcccg ccccaggtaa | | | 180 |
| gctggtgtgg tggggttggc aaggacagtc tccccgggag cctgggggca agcaggcaga | | | 240 |
| ggccagctcg ggaccagcac ctgtgtgcca gggacaaggg tggggaggtc gagcccagcg | | | 300 |
| ggagctgggt gcactgcatg ggctctttcg ggtggctgct tgcctgcttc ccggcagctg | | | 360 |
| gttccagggc tggagaccca gtgtgctatg ccccaggttc ccagccaagg cattccggtg | | | 420 |
| aagggggctgg accccgccaa ggtgcggtcc ctgagctgcc tctgcctctc caatccctg | | | 480 |
| ctggggactg tggctggagg caggcagtag agcgctctga ggcctgcctt ttctgttcag | | | 540 |
| taggtgacag gagtggggct gacgctccca gagccaaagg tcacaggtgc tgtggtcggg | | | 600 |
| ggtggcagga agtgagcccc agaagggtca gagctttggc tagggggagg atggtacaca | | | 660 |
| gcagggcccg ggcgaacccc tctctccagt cctcagggtt tgtgcctctc gctcggacag | | | 720 |
| tttgaggact tgctatcccc gtgggaacat cacc atg tcc gag gca ccc cgg gcc | | | 775 |
| | | Met Ser Glu Ala Pro Arg Ala | |
| | | 1               5 | |

```
gag acc ttt gtc ttc ctg gac ctg gaa gcc act ggg ctc ccc agt gtg       823
Glu Thr Phe Val Phe Leu Asp Leu Glu Ala Thr Gly Leu Pro Ser Val
        10                  15                  20 gag ccc gag att gcc gag ctg tcc ctc ttt gct gtc cac cgc tcc tcc       871
Glu Pro Glu Ile Ala Glu Leu Ser Leu Phe Ala Val His Arg Ser Ser
    25                  30                  35 ctg gag aac ccg gag cac gac gag tct ggt gcc cta gta ttg ccc cgg       919
Leu Glu Asn Pro Glu His Asp Glu Ser Gly Ala Leu Val Leu Pro Arg
40                  45                  50                  55 gtc ctg gac aag ctc acg ctg tgc atg tgc ccg gag cgc ccc ttc act       967
Val Leu Asp Lys Leu Thr Leu Cys Met Cys Pro Glu Arg Pro Phe Thr
            60                  65                  70 gcc aag gcc agc gag atc acc ggc ctg agc agt gag ggc ctg gcg cga      1015
Ala Lys Ala Ser Glu Ile Thr Gly Leu Ser Ser Glu Gly Leu Ala Arg
    75                  80                  85
```

-continued

```
tgc cgg aag gct ggc ttt gat ggc gcc gtg gtg cgg acg ctg cag gcc    1063
Cys Arg Lys Ala Gly Phe Asp Gly Ala Val Val Arg Thr Leu Gln Ala
        90                  95                 100 ttc ctg agc cgc cag gca ggg ccc atc tgc ctt gtg gcc cac aat ggc    1111
Phe Leu Ser Arg Gln Ala Gly Pro Ile Cys Leu Val Ala His Asn Gly
    105                 110                 115 ttt gat tat gat ttc ccc ctg ctg tgt gcc gag ctg cgg cgc ctg ggt    1159
Phe Asp Tyr Asp Phe Pro Leu Leu Cys Ala Glu Leu Arg Arg Leu Gly
120                 125                 130                 135 gcc cgc ctg ccc cgg gac act gtc tgc ctg gac acg ctg ccg gcc ctg    1207
Ala Arg Leu Pro Arg Asp Thr Val Cys Leu Asp Thr Leu Pro Ala Leu
            140                 145                 150 cgg ggc ctg gac cgc gcc cac agc cac ggc acc cgg gcc cgg ggc cgc    1255
Arg Gly Leu Asp Arg Ala His Ser His Gly Thr Arg Ala Arg Gly Arg
        155                 160                 165 cag ggt tac agc ctc ggc agc ctc ttc cac cgc tac ttc cgg gca gag    1303
Gln Gly Tyr Ser Leu Gly Ser Leu Phe His Arg Tyr Phe Arg Ala Glu
    170                 175                 180 cca agc gca gcc cac tca gcc gag ggc gac gtg cac acc ctg ctc ctg    1351
Pro Ser Ala Ala His Ser Ala Glu Gly Asp Val His Thr Leu Leu Leu
    185                 190                 195 atc ttc ctg cac cgc gcc gca gag ctg ctc gcc tgg gcc gat gag cag    1399
Ile Phe Leu His Arg Ala Ala Glu Leu Leu Ala Trp Ala Asp Glu Gln
200                 205                 210                 215 gcc cgt ggg tgg gcc cac atc gag ccc atg tac ttg ccg cct gat gac    1447
Ala Arg Gly Trp Ala His Ile Glu Pro Met Tyr Leu Pro Pro Asp Asp
            220                 225                 230 ccc agc ctg gag gcc tgagcaccag ggccacctcc tgtgccatgg acagtgccag    1502
Pro Ser Leu Glu Ala
            235 cctccaccgt tcagctggcc tctaccaccc ccggctcctc ctatctgggc agcctcaggt    1562 ccgtgcacct gccaggcctt ccctggctgc ctgaccagcc atacggccct ggattcctct    1622 ccaggccccg cttccaggac cgtgctctcc cggctggcct gggtgcccag cagagtttgc    1682 tgtttcccaa taaacattgc caactactca ccctc                               1717
```

<210> SEQ ID NO 4
<211> LENGTH: 236
<212> TYPE: PRT
<213> ORGANISM: HOMO SAPIENS

<400> SEQUENCE: 4

```
Met Ser Glu Ala Pro Arg Ala Glu Thr Phe Val Phe Leu Asp Leu Glu
 1               5                  10                  15

Ala Thr Gly Leu Pro Ser Val Glu Pro Glu Ile Ala Glu Leu Ser Leu
                20                  25                  30

Phe Ala Val His Arg Ser Ser Leu Glu Asn Pro Glu His Asp Glu Ser
            35                  40                  45

Gly Ala Leu Val Leu Pro Arg Val Leu Asp Lys Leu Thr Leu Cys Met
        50                  55                  60

Cys Pro Glu Arg Pro Phe Thr Ala Lys Ala Ser Glu Ile Thr Gly Leu
65                  70                  75                  80

Ser Ser Glu Gly Leu Ala Arg Cys Arg Lys Ala Gly Phe Asp Gly Ala
                85                  90                  95

Val Val Arg Thr Leu Gln Ala Phe Leu Ser Arg Gln Ala Gly Pro Ile
            100                 105                 110

Cys Leu Val Ala His Asn Gly Phe Asp Tyr Asp Phe Pro Leu Leu Cys
```

```
            115                 120                 125
Ala Glu Leu Arg Arg Leu Gly Ala Arg Leu Pro Arg Asp Thr Val Cys
        130                 135                 140

Leu Asp Thr Leu Pro Ala Leu Arg Gly Leu Asp Arg Ala His Ser His
145                 150                 155                 160

Gly Thr Arg Ala Arg Gly Arg Gln Gly Tyr Ser Leu Gly Ser Leu Phe
                165                 170                 175

His Arg Tyr Phe Arg Ala Glu Pro Ser Ala Ala His Ser Ala Glu Gly
            180                 185                 190

Asp Val His Thr Leu Leu Ile Phe Leu His Arg Ala Ala Glu Leu
        195                 200                 205

Leu Ala Trp Ala Asp Glu Gln Ala Arg Gly Trp Ala His Ile Glu Pro
    210                 215                 220

Met Tyr Leu Pro Pro Asp Asp Pro Ser Leu Glu Ala
225                 230                 235

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence:peptide

<400> SEQUENCE: 5

Ala Phe Asp Ala Asp Leu Asn Leu Ile Arg
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence:peptide

<400> SEQUENCE: 6

Tyr Ala Leu Glu Leu Ser Ala Pro Gln Gly Pro Ser Pro Thr Ala Pro
1               5                   10                  15

Val

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence:peptide

<400> SEQUENCE: 7

Ala Leu Glu Pro Thr Gly Ser Ser Ser Glu His Gly Pro Arg
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:peptide
<221> NAME/KEY: UNSURE
<222> LOCATION: (1)
<221> NAME/KEY: UNSURE
<222> LOCATION: (6)
<221> NAME/KEY: UNSURE
<222> LOCATION: (9)

<400> SEQUENCE: 8
```

Xaa Tyr Asp Leu Gly Xaa Val Tyr Xaa
 1               5

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:cDNA

<400> SEQUENCE: 9
tagcatgaat tctaygcnyt ngargg                                          26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:cDNA

<400> SEQUENCE: 10
gcatcaggat cctcngcrtc raangc                                          26

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence:cDNA

<400> SEQUENCE: 11
tcagcagaat tcgcnytnga rggnytnwsn gcnccncarg g                         41

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence:cDNA

<400> SEQUENCE: 12
ggtgttggag ccncknatna rrttnagnar rtcngcrtc                            39

<210> SEQ ID NO 13
<211> LENGTH: 485
<212> TYPE: DNA
<213> ORGANISM: Artificial Sequence
<220> FEATURE:
<223> OTHER INFORMATION: Description of Artificial Sequence:cDNA

<400> SEQUENCE: 13
cgtgagccga gtcactactg cctgcctgcc tgcctgctac gcccaaggtc acggagctgt     60
gcctgctggc tgtccacaga tgtgccctgg agagcccccc cacctctcag gggccacctc    120
ccacagttcc tccaccaccg cgtgtggtag acaagctctc cctgtgtgtg gctccgggga    180
aggcctgcag ccctgcagcc agcgagatca caggtctgag cacagctgtg tggcagcgca    240
tgggcgtcaa tgttttgatg acaacctggc caacctgctc ctagccttcc tgcggcgcca    300
cactagcctc tggtgcctgg tggacagcaa tggtgaccgc tacgacttcc ccctgctcca    360
agcagagctg gctatgctgg gcctcaccag tgctctggat ggtgccttct gtgtggatag    420
catcactgcg ctgaaggccc tggagcgagc aagcagcccc tcagaacacg gcccaaggaa    480
gagct                                                                485

<210> SEQ ID NO 14
<211> LENGTH: 467
<212> TYPE: DNA
<213> ORGANISM: Artificial Sequence
<220> FEATURE:
<223> OTHER INFORMATION: Description of Artificial Sequence:cDNA

<400> SEQUENCE: 14

| | | | | | |
|---|---|---|---|---|---|
| tttttttttt | ttatggggca | gcggggtct | ttattcgtca | gatttttcctt | cttggcctac | 60 |
| tccccaggtg | tggccaggga | tagtccatac | agtgtggcta | ctgccaaggt | caggatggcc | 120 |
| agcagaccca | gtggggccag | cagccctctc | ctggataggg | ctccagggtc | cttcactgga | 180 |
| ggaagatcct | tggtacccct | gctctctcca | aggctggac | tagtgttcct | ggttgtggcc | 240 |
| aggtgtgcag | tggttgtgac | agcagatggt | cttggcttgg | tcctagcaga | ggctgtgacc | 300 |
| ccatacatgg | gcctgatggt | gccgaaacgc | tggcgtgacg | atccaccac | cgcagcaggg | 360 |
| cctgtggtct | ccactgacag | atgctgagca | gggccaggac | atcaccctca | gccgtgtgcg | 420 |
| agtctggagg | ggactgccca | tacaggcgag | tgtagatgct | gcctagg | | 467 |

<210> SEQ ID NO 15
<211> LENGTH: 403
<212> TYPE: DNA
<213> ORGANISM: Artificial Sequence
<220> FEATURE:
<223> OTHER INFORMATION: Description of Artificial Sequence:cDNA

<400> SEQUENCE: 15

| | | | | | |
|---|---|---|---|---|---|
| gagagtgtgc | agccgagtca | ctactgcctg | cctgcctgcc | tgctacgccc | aaggtcacgg | 60 |
| agctgtgcct | gctggctgtc | cacagatgtg | ccctggagag | cccccccacc | tctcagggc | 120 |
| cacctcccac | agttcctcca | ccaccgcgtg | tggtagacaa | gctctccctg | tgtgtggctc | 180 |
| cggggaaggc | ctgcagccct | gcagccagcg | agatcacagg | tctgagcaca | gctgtgtggg | 240 |
| cagcgcatgg | gcgttcaatg | ttttgatgac | aacctgggcc | aacctgnttc | ctagccttcc | 300 |
| tgcgggcgcc | anaccaggcc | ctgggtgcct | gggttggaaa | acaaatnggt | gaaccgntta | 360 |
| cggactttnc | cccttgttcc | aaggcagagt | tgggcttatt | gtt | | 403 |

<210> SEQ ID NO 16
<211> LENGTH: 185
<212> TYPE: DNA
<213> ORGANISM: Artificial Sequence
<220> FEATURE:
<223> OTHER INFORMATION: Description of Artificial Sequence:cDNA

<400> SEQUENCE: 16

| | | | | | |
|---|---|---|---|---|---|
| tggggcagcg | ggggtcttta | ttcgtcagat | tttccttctt | ggcctactcc | ccaggttggc | 60 |
| cagggatagt | ccatacagtt | ggctactgca | aggtcaggat | ggccagcaga | cccagtgggg | 120 |
| ccagcagccc | ctccctggat | agggctccag | ggtccttcac | tggaggaaga | tccttggtac | 180 |
| ccctg | | | | | | 185 |

<210> SEQ ID NO 17
<211> LENGTH: 487
<212> TYPE: DNA
<213> ORGANISM: Artificial Sequence
<220> FEATURE:
<223> OTHER INFORMATION: Description of Artificial Sequence:cDNA

<400> SEQUENCE: 17

```
gagggacagg gcagaccaag aattgatgag atgactcctg ctggagttga gagggccccc      60
atggttcagc atgggctcac agaccctgcc ccatggtcac atgcagaccc tcatcttctt     120
agacctggaa gccactggcc tgccttcgtc tcggcccgaa gtcacagagc tgtgcctgct     180
ggctgtccac agacgtgctc tggagaacac ttccatttct cagggacatc cacctccagt     240
gcccagaccg ccccgtgtgg tggacaagct ctctctgtgc attgctccag ggaaagcctg     300
tagccctggg gccagtgaga tcacaggtct gagcaaagct gagctggaag tacaggggcg     360
tcaacgcttc gatgacaacc tggccatcct gctccgagcc ttcctgcagc gccagcacag     420
ccttgctgcc ttgtggcaca acggtgac cgctatgact ttcctctgct ccagacagag       480
cttgcta                                                               487

<210> SEQ ID NO 18
<211> LENGTH: 395
<212> TYPE: DNA
<213> ORGANISM: Artificial Sequence
<220> FEATURE:
<223> OTHER INFORMATION: Description of Artificial Sequence:cDNA

<400> SEQUENCE: 18 aactttagg tagtgggtgg ccaagcaaga ccaggtggta ctgatagata caacagaact       60
tacagtggca tcagtggagg ggtccaggat cttaatttct cagaccttgc atctctcctt    120
cagcatggaa atccagtcag cttgaaaact ggcatccaag agtccttcat ttctcaaacc    180
ctgcctgccc tattgtgagg aagtaggagc tggggatttc aaggtatttg atggtcacaa    240
agttctgtga ctgtaaaagt aggaattagt cgtctttcca gtccttttgg gaaacgactc    300
acagactgcg ataggtagaa tgccttactc catcttctca agttcctttg ccctgtaca    360 ttttgaatct ttcatttcca ctgtagacaa cactc                                395

<210> SEQ ID NO 19
<211> LENGTH: 139
<212> TYPE: DNA
<213> ORGANISM: Artificial Sequence
<220> FEATURE:
<223> OTHER INFORMATION: Description of Artificial Sequence:cDNA

<400> SEQUENCE: 19
tttttttttt tttttttttt atggggcagc gggggtcttt attcgtcaga ttttccttct     60
tggcctactc cccaggtgtg gccagggata gtccatacag tgtggctact gcaaggtcag    120
gatggccagc agacccagt                                                  139

<210> SEQ ID NO 20
<211> LENGTH: 277
<212> TYPE: DNA
<213> ORGANISM: Artificial Sequence
<220> FEATURE:
<223> OTHER INFORMATION: Description of Artificial Sequence:cDNA

<400> SEQUENCE: 20
tgaaagggcc gcagcagggg ctcccagcag tgtgtaagac cgggagctgg tctggcacca     60 ctgcctggt ccttccagct gcctgtcact ggtatgatgg cccgtgca ttgtgccacc      120 agcaggccac agctgtggat cttggaaggc ctctggggtc ccccgggagc aggggatggt    180
ttgggggaag gatgttgtta aaaggacaga ccaggcaggc cctgccccgg ggccatgcag    240
accctcatct ttttcgacat ggaggccact ggcttgc                              277
```

```
<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence:cDNA

<400> SEQUENCE: 21
actcatacgt cgacaggagg taaaaaaaaa tgcagaccct catct            45

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence:cDNA

<400> SEQUENCE: 22
gtaaaacgac ggccagt                                           17

<210> SEQ ID NO 23
<211> LENGTH: 287
<212> TYPE: DNA
<213> ORGANISM: Artificial Sequence
<220> FEATURE:
<223> OTHER INFORMATION: Description of Artificial Sequence:cDNA

<400> SEQUENCE: 23
ggcacgaggg gaagccagct gaagcccgcc ccagctctag gcctcattgt tcctgtaaga    60
acatcaacat gtctgagcca ccccgggctg agacctttgt attcctggac ctagaagcca   120
ctgggctccc aaacatggat cctgagattg cagagatatc cctttttgct gttcaccgct   180
cttccctgga gaacccagaa cgggatgatt ctggttcctt ggtgctgccc cgtgttctgg   240
acaagctcac actgtgcatg tgcccggagc gcccctttac tgccaag              287

<210> SEQ ID NO 24
<211> LENGTH: 320
<212> TYPE: DNA
<213> ORGANISM: Artificial Sequence
<220> FEATURE:
<223> OTHER INFORMATION: Description of Artificial Sequence:cDNA

<400> SEQUENCE: 24
ccaagccagt gagcccctgc cttggaagta aaggataaa ggtgagacgg ggttattatt     60
tatggctcag tggtagagca gttgcctaat aagtcagcag atcctgcatt caatcccaag   120
atcccacccc ctgaaaatag ttccttattt cttttctctt atttatttct tgagacaaga   180
gtatcactgt gtcaacttga ctggcctgga acttgctatg gagaccaagt ttggccttga   240
cctcaccgag aaccctctga ttctgcctcc acactgctga gattaaagcc aggtgccacc   300
acctgcggca cacatagttc                                              320

<210> SEQ ID NO 25
<211> LENGTH: 41
<212> TYPE: DNA
<213> ORGANISM: Artificial Sequence
<220> FEATURE:
<223> OTHER INFORMATION: Description of Artificial Sequence:cDNA

<400> SEQUENCE: 25
gcgtcaagct tgggaacatc accatgtccg aggcaccccg g                 41

<210> SEQ ID NO 26
```

```
<211> LENGTH: 41
<212> TYPE: DNA
<213> ORGANISM: Artificial Sequence
<220> FEATURE:
<223> OTHER INFORMATION: Description of Artificial Sequence:cDNA

<400> SEQUENCE: 26
gtcgcggatc ctggccctgg tgctcaggcc tccaggctgg g                 41

<210> SEQ ID NO 27
<211> LENGTH: 47
<212> TYPE: DNA
<213> ORGANISM: Artificial Sequence
<220> FEATURE:
<223> OTHER INFORMATION: Description of Artificial Sequence:cDNA

<400> SEQUENCE: 27
agtgatacag tcgacaggag gtaaaaaaaa atgtctgagc caccccg           47

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence:cDNA

<400> SEQUENCE: 28
actcatacgt cgacaggagg taaaaaaaaa tggtctcagc ggatg             45

<210> SEQ ID NO 29
<211> LENGTH: 1058
<212> TYPE: DNA
<213> ORGANISM: Mus musculus
<220> FEATURE:
<221> NAME/KEY: CDS
<222> LOCATION: (71)..(1012)

<400> SEQUENCE: 29
gagggacagg gcagaccaag aattgatgag atgactcctg ctggagttga gagggccccc    60
atggttcagc atg ggc tca cag acc ctg ccc cat ggt cac atg cag acc       109
            Met Gly Ser Gln Thr Leu Pro His Gly His Met Gln Thr
              1               5                  10 ctc atc ttc tta gac ctg gaa gcc act ggc ctg cct tcg tct cgg ccc      157
Leu Ile Phe Leu Asp Leu Glu Ala Thr Gly Leu Pro Ser Ser Arg Pro
 15                  20                  25 gaa gtc aca gag ctg tgc ctg ctg gct gtc cac aga cgt gct ctg gag      205
Glu Val Thr Glu Leu Cys Leu Leu Ala Val His Arg Arg Ala Leu Glu
 30                  35                  40                  45 aac act tcc att tct cag gga cat cca cct cca gtg ccc aga ccg ccc      253
Asn Thr Ser Ile Ser Gln Gly His Pro Pro Pro Val Pro Arg Pro Pro
                 50                  55                  60 cgt gtg gtg gac aag ctc tct ctg tgc att gct cca ggg aaa gcc tgt      301
Arg Val Val Asp Lys Leu Ser Leu Cys Ile Ala Pro Gly Lys Ala Cys
             65                  70                  75 agc cct ggg gcc agt gag atc aca ggt ctg agc aaa gct gag ctg gaa      349
Ser Pro Gly Ala Ser Glu Ile Thr Gly Leu Ser Lys Ala Glu Leu Glu
         80                  85                  90 gta cag ggg cgt caa cgc ttc gat gac aac ctg gcc atc ctg ctc cga      397
Val Gln Gly Arg Gln Arg Phe Asp Asp Asn Leu Ala Ile Leu Leu Arg
     95                  100                 105 gcc ttc ctg cag cgc cag cca cag cct tgc tgc ctt gtg gca cac aac      445
Ala Phe Leu Gln Arg Gln Pro Gln Pro Cys Cys Leu Val Ala His Asn
110                 115                 120                 125
```

-continued

```
ggt gac cgc tat gac ttt cct ctg ctc cag aca gag ctt gct agg ctg      493
Gly Asp Arg Tyr Asp Phe Pro Leu Leu Gln Thr Glu Leu Ala Arg Leu
                130                 135                 140
agc act ccc agt ccc cta gat ggt acc ttc tgt gtg gac agc atc gct      541
Ser Thr Pro Ser Pro Leu Asp Gly Thr Phe Cys Val Asp Ser Ile Ala
            145                 150                 155
gcc cta aag gcc ttg gaa caa gct agc agc ccc tca ggg aat ggt tcg      589
Ala Leu Lys Ala Leu Glu Gln Ala Ser Ser Pro Ser Gly Asn Gly Ser
        160                 165                 170
agg aaa agc tac agc ctg ggc agc atc tac acc cgc ctg tac tgg caa      637
Arg Lys Ser Tyr Ser Leu Gly Ser Ile Tyr Thr Arg Leu Tyr Trp Gln
    175                 180                 185
gca ccg aca gac tca cat act gct gaa ggt gat gtt cta acc ctg ctc      685
Ala Pro Thr Asp Ser His Thr Ala Glu Gly Asp Val Leu Thr Leu Leu
190                 195                 200                 205
agc atc tgt cag tgg aag cca cag gcc cta ctg cag tgg gtg gac gaa      733
Ser Ile Cys Gln Trp Lys Pro Gln Ala Leu Leu Gln Trp Val Asp Glu
                210                 215                 220
cat gcc cgg ccc ttt agc acc gtc aag ccc atg tac ggc act ccg gct      781
His Ala Arg Pro Phe Ser Thr Val Lys Pro Met Tyr Gly Thr Pro Ala
            225                 230                 235
acc act gga aca acc aac cta agg cca cat gct gcc aca gct act aca      829
Thr Thr Gly Thr Thr Asn Leu Arg Pro His Ala Ala Thr Ala Thr Thr
        240                 245                 250
ccc ctg gcc aca gcc aat gga agt ccc agc aat ggc agg agc agg cga      877
Pro Leu Ala Thr Ala Asn Gly Ser Pro Ser Asn Gly Arg Ser Arg Arg
    255                 260                 265
cct aag agt cct cct cca gag aag gtc cca gaa gcc cca tca cag gag      925
Pro Lys Ser Pro Pro Pro Glu Lys Val Pro Glu Ala Pro Ser Gln Glu
270                 275                 280                 285
ggg ctg ttg gcc cca ctg agc ctg ctg acc ctc ctg acc ttg gca ata      973
Gly Leu Leu Ala Pro Leu Ser Leu Leu Thr Leu Leu Thr Leu Ala Ile
                290                 295                 300
gcc act ctg tat gga ctc ttc ctg gcc tca cct ggg cag taagtcaaga      1022
Ala Thr Leu Tyr Gly Leu Phe Leu Ala Ser Pro Gly Gln
            305                 310
ggggaaatat gatgaataaa gacttccata gcactg                             1058

<210> SEQ ID NO 30
<211> LENGTH: 314
<212> TYPE: PRT
<213> ORGANISM: Mus musculus

<400> SEQUENCE: 30

Met Gly Ser Gln Thr Leu Pro His Gly His Met Gln Thr Leu Ile Phe
  1               5                  10                  15

Leu Asp Leu Glu Ala Thr Gly Leu Pro Ser Ser Arg Pro Glu Val Thr
             20                  25                  30

Glu Leu Cys Leu Leu Ala Val His Arg Arg Ala Leu Glu Asn Thr Ser
         35                  40                  45

Ile Ser Gln Gly His Pro Pro Pro Val Pro Arg Pro Pro Arg Val Val
     50                  55                  60

Asp Lys Leu Ser Leu Cys Ile Ala Pro Gly Lys Ala Cys Ser Pro Gly
 65                  70                  75                  80

Ala Ser Glu Ile Thr Gly Leu Ser Lys Ala Glu Leu Glu Val Gln Gly
                 85                  90                  95

Arg Gln Arg Phe Asp Asp Asn Leu Ala Ile Leu Leu Arg Ala Phe Leu
            100                 105                 110

Gln Arg Gln Pro Gln Pro Cys Cys Leu Val Ala His Asn Gly Asp Arg
```

```
                115                 120                     125
Tyr Asp Phe Pro Leu Leu Gln Thr Glu Leu Ala Arg Leu Ser Thr Pro
    130                 135                 140

Ser Pro Leu Asp Gly Thr Phe Cys Val Asp Ser Ile Ala Ala Leu Lys
145                 150                 155                 160

Ala Leu Glu Gln Ala Ser Ser Pro Ser Gly Asn Gly Ser Arg Lys Ser
                165                 170                 175

Tyr Ser Leu Gly Ser Ile Tyr Thr Arg Leu Tyr Trp Gln Ala Pro Thr
            180                 185                 190

Asp Ser His Thr Ala Glu Gly Asp Val Leu Thr Leu Leu Ser Ile Cys
        195                 200                 205

Gln Trp Lys Pro Gln Ala Leu Leu Gln Trp Val Asp Glu His Ala Arg
    210                 215                 220

Pro Phe Ser Thr Val Lys Pro Met Tyr Gly Thr Pro Ala Thr Thr Gly
225                 230                 235                 240

Thr Thr Asn Leu Arg Pro His Ala Ala Thr Ala Thr Pro Leu Ala
                245                 250                 255

Thr Ala Asn Gly Ser Pro Ser Asn Gly Arg Ser Arg Pro Lys Ser
                260                 265                 270

Pro Pro Pro Glu Lys Val Pro Glu Ala Pro Ser Gln Glu Gly Leu Leu
                275                 280                 285

Ala Pro Leu Ser Leu Leu Thr Leu Leu Thr Leu Ala Ile Ala Thr Leu
    290                 295                 300

Tyr Gly Leu Phe Leu Ala Ser Pro Gly Gln
305                 310
```

<210> SEQ ID NO 31
<211> LENGTH: 1003
<212> TYPE: DNA
<213> ORGANISM: Mus musculus
<220> FEATURE:
<221> NAME/KEY: CDS
<222> LOCATION: (69)..(776)

<400> SEQUENCE: 31

```
ggcacgaggg gaagccagct gaagcccgcc ccagctctag gcctcattgt tcctgtaaga     60 acatcaac atg tct gag cca ccc cgg gct gag acc ttt gta ttc ctg gac    110
         Met Ser Glu Pro Pro Arg Ala Glu Thr Phe Val Phe Leu Asp
           1               5                  10 cta gaa gcc act ggg ctc cca aac atg gat cct gag att gca gag ata     158
Leu Glu Ala Thr Gly Leu Pro Asn Met Asp Pro Glu Ile Ala Glu Ile
 15                  20                  25                  30 tcc ctt ttt gct gtt cac cgc tct tct ctg gag aac cca gaa cgg gat     206
Ser Leu Phe Ala Val His Arg Ser Ser Leu Glu Asn Pro Glu Arg Asp
                 35                  40                  45 gat tct ggt tcc ttg gtg ctg ccc cgt gtt ctg gac aag ctc aca ctg     254
Asp Ser Gly Ser Leu Val Leu Pro Arg Val Leu Asp Lys Leu Thr Leu
             50                  55                  60 tgc atg tgc ccg gag cgc ccc ttt act gcc aag gcc agt gag att act     302
Cys Met Cys Pro Glu Arg Pro Phe Thr Ala Lys Ala Ser Glu Ile Thr
         65                  70                  75 ggt ttg agc agc gaa agc ctg atg cac tgc ggg aag gct ggt ttc aat     350
Gly Leu Ser Ser Glu Ser Leu Met His Cys Gly Lys Ala Gly Phe Asn
     80                  85                  90 ggc gct gtg gta agg aca ctg cag ggc ttc cta agc cgc cag gag ggc     398
Gly Ala Val Val Arg Thr Leu Gln Gly Phe Leu Ser Arg Gln Glu Gly
 95                 100                 105                 110
```

```
ccc atc tgc ctt gtg gcc cac aat ggc ttc gat tat gac ttc cca ctg      446
Pro Ile Cys Leu Val Ala His Asn Gly Phe Asp Tyr Asp Phe Pro Leu
            115                 120                 125 ctg tgc acg gag cta caa cgt ctg ggt gcc cat ctg ccc caa gac act      494
Leu Cys Thr Glu Leu Gln Arg Leu Gly Ala His Leu Pro Gln Asp Thr
130                 135                 140 gtc tgc ctg gac aca ctg cct gca ttg cgg ggc ctg gac cgg gct cac      542
Val Cys Leu Asp Thr Leu Pro Ala Leu Arg Gly Leu Asp Arg Ala His
            145                 150                 155 agc cac ggc acc agg gct caa ggc cgc aaa agc tac agc ctg gcc agt      590
Ser His Gly Thr Arg Ala Gln Gly Arg Lys Ser Tyr Ser Leu Ala Ser
160                 165                 170 ctc ttc cac cgc tac ttc cag gct gaa ccc agt gct gcc cat tca gca      638
Leu Phe His Arg Tyr Phe Gln Ala Glu Pro Ser Ala Ala His Ser Ala
175                 180                 185                 190 gaa ggt gat gtg cac acc ctg ctt ctg atc ttc ctg cat cgt gct cct      686
Glu Gly Asp Val His Thr Leu Leu Leu Ile Phe Leu His Arg Ala Pro
                195                 200                 205 gag ctg ctc gcc tgg gca gat gag cag gcc cgc agc tgg gct cat att      734
Glu Leu Leu Ala Trp Ala Asp Glu Gln Ala Arg Ser Trp Ala His Ile
            210                 215                 220 gag ccc atg tac gtg cca cct gat ggt cca agc ctc gaa gcc                776
Glu Pro Met Tyr Val Pro Pro Asp Gly Pro Ser Leu Glu Ala
225                 230                 235 tgaatgccag tgccatccat tcatccaggc tctgagctac atctttgctc tctgtagcac      836
ctttgtggcc ttcctcagcc ctgacctacc tggcctagg atcctacagc cttctctgta       896
ctccactatc agttgggcac cttctggcca gcctgtgagt tgctctttca gggcttccat      956 cttctcatccc atttctcaat aaatatcacc aactatttac cagctga                  1003

<210> SEQ ID NO 32
<211> LENGTH: 236
<212> TYPE: PRT
<213> ORGANISM: Mus musculus

<400> SEQUENCE: 32

Met Ser Glu Pro Pro Arg Ala Glu Thr Phe Val Phe Leu Asp Leu Glu
1               5                   10                  15

Ala Thr Gly Leu Pro Asn Met Asp Pro Glu Ile Ala Glu Ile Ser Leu
            20                  25                  30

Phe Ala Val His Arg Ser Ser Leu Glu Asn Pro Glu Arg Asp Asp Ser
        35                  40                  45

Gly Ser Leu Val Leu Pro Arg Val Leu Asp Lys Leu Thr Leu Cys Met
    50                  55                  60

Cys Pro Glu Arg Pro Phe Thr Ala Lys Ala Ser Glu Ile Thr Gly Leu
65                  70                  75                  80

Ser Ser Glu Ser Leu Met His Cys Gly Lys Ala Gly Phe Asn Gly Ala
                85                  90                  95

Val Val Arg Thr Leu Gln Gly Phe Leu Ser Arg Gln Glu Gly Pro Ile
            100                 105                 110

Cys Leu Val Ala His Asn Gly Phe Asp Tyr Asp Phe Pro Leu Leu Cys
        115                 120                 125

Thr Glu Leu Gln Arg Leu Gly Ala His Leu Pro Gln Asp Thr Val Cys
    130                 135                 140

Leu Asp Thr Leu Pro Ala Leu Arg Gly Leu Asp Arg Ala His Ser His
145                 150                 155                 160

Gly Thr Arg Ala Gln Gly Arg Lys Ser Tyr Ser Leu Ala Ser Leu Phe
```

```
                          165                 170                 175
His Arg Tyr Phe Gln Ala Glu Pro Ser Ala Ala His Ser Ala Glu Gly
                180                 185                 190

Asp Val His Thr Leu Leu Leu Ile Phe Leu His Arg Ala Pro Glu Leu
            195                 200                 205

Leu Ala Trp Ala Asp Glu Gln Ala Arg Ser Trp Ala His Ile Glu Pro
        210                 215                 220

Met Tyr Val Pro Pro Asp Gly Pro Ser Leu Glu Ala
225                 230                 235

<210> SEQ ID NO 33
<211> LENGTH: 1296
<212> TYPE: DNA
<213> ORGANISM: Drosophila melanogaster
<220> FEATURE:
<221> NAME/KEY: CDS
<222> LOCATION: (93)..(1145)
<400> SEQUENCE: 33
agaactccgt gttggtcctc aaacattttg aataaaacga aatatatgta catactatgt      60
acatgcactt ttagccacca gttgcgctct ta atg gct ccg aac gat gca gtt     113
                                    Met Ala Pro Asn Asp Ala Val
                                     1               5 gcg gag cac gcg gag gag cag cca aag att tcc aca ttt gcc gtt ctg    161
Ala Glu His Ala Glu Glu Gln Pro Lys Ile Ser Thr Phe Ala Val Leu
            10                  15                  20 gac cta gag acc acc aac ttg cct gcc tac agg aac aac cga gtg agc    209
Asp Leu Glu Thr Thr Asn Leu Pro Ala Tyr Arg Asn Asn Arg Val Ser
        25                  30                  35 att acg gag ttg tgc att tac gcc ttt gaa gcc gcg ctc ctt aag aag    257
Ile Thr Glu Leu Cys Ile Tyr Ala Phe Glu Ala Ala Leu Leu Lys Lys
 40                  45                  50                  55 aaa aag aag gag cag gac cag gat gag cag cag gag ctg cca gcg gca    305
Lys Lys Lys Glu Gln Asp Gln Asp Glu Gln Gln Glu Leu Pro Ala Ala
                 60                  65                  70 ccg cgg gtg ctg cac aaa ttg aat gtg ctc ttc cag ccg tcc atg gta    353
Pro Arg Val Leu His Lys Leu Asn Val Leu Phe Gln Pro Ser Met Val
             75                  80                  85 gtg gac ccg gaa gcg gag aga ata aca ggt ctg agc aac tac ttg ctg    401
Val Asp Pro Glu Ala Glu Arg Ile Thr Gly Leu Ser Asn Tyr Leu Leu
         90                  95                 100 gag cgg gag tcc cag cta gac acg gat gcc gcg caa ctc atc gtc agt    449
Glu Arg Glu Ser Gln Leu Asp Thr Asp Ala Ala Gln Leu Ile Val Ser
     105                 110                 115 ttt cta aag cac ttg ccg agt ccg gtt tgc ctg gtg gct cac aat ggt    497
Phe Leu Lys His Leu Pro Ser Pro Val Cys Leu Val Ala His Asn Gly
120                 125                 130                 135 tgg ggc ttc gat ttt ccc att ctg agg cag gca ttt gag aaa cta aac    545
Trp Gly Phe Asp Phe Pro Ile Leu Arg Gln Ala Phe Glu Lys Leu Asn
                140                 145                 150 ata gag ctt ccc caa tcc ctg act tgt gtt gac tca ctg cgc gcc ttc    593
Ile Glu Leu Pro Gln Ser Leu Thr Cys Val Asp Ser Leu Arg Ala Phe
            155                 160                 165 atg gag att gac gac aca caa caa aaa gaa acc agt cag ttg aaa gta    641
Met Glu Ile Asp Asp Thr Gln Gln Lys Glu Thr Ser Gln Leu Lys Val
        170                 175                 180 ccc aac gat gtg cag gaa atc att ccg gag ctg aaa ccc aaa cag aat    689
Pro Asn Asp Val Gln Glu Ile Ile Pro Glu Leu Lys Pro Lys Gln Asn
    185                 190                 195 act gaa act tgc ctc aag gag cca gaa gcg gtc gtg aac atc gat tgg    737
```

```
Thr Glu Thr Cys Leu Lys Glu Pro Glu Ala Val Val Asn Ile Asp Trp
200                 205                 210                 215 cga acc aga aac gaa acc act cca aat cgt cca att tta aag cct aca       785
Arg Thr Arg Asn Glu Thr Thr Pro Asn Arg Pro Ile Leu Lys Pro Thr
                220                 225                 230 gag gca ttc gcc aag cgt aag tta tta cgc gac ggc gat gag gat gac       833
Glu Ala Phe Ala Lys Arg Lys Leu Leu Arg Asp Gly Asp Glu Asp Asp
            235                 240                 245 ttg gag gag cag acc cct ccc aag cgg aaa ccc gat gag ttt agg tca       881
Leu Glu Glu Gln Thr Pro Pro Lys Arg Lys Pro Asp Glu Phe Arg Ser
        250                 255                 260 cga cgc cag ctg ttc agt gga tgc aag tgt gcc gag aac aaa cgc tat       929
Arg Arg Gln Leu Phe Ser Gly Cys Lys Cys Ala Glu Asn Lys Arg Tyr
    265                 270                 275 ccc ccc cgc gga gtt tat aat ttg gaa agt ctc tac acg aga ata ttt       977
Pro Pro Arg Gly Val Tyr Asn Leu Glu Ser Leu Tyr Thr Arg Ile Phe
280                 285                 290                 295 aag ata cca gca ctt agt gct cac cag gca gag gct gat gta gtc atg      1025
Lys Ile Pro Ala Leu Ser Ala His Gln Ala Glu Ala Asp Val Val Met
                300                 305                 310 acc aca aaa ctg ata cag cat tac ggc att gat ttc ctg gcc ttc gcc      1073
Thr Thr Lys Leu Ile Gln His Tyr Gly Ile Asp Phe Leu Ala Phe Ala
                315                 320                 325 gag gag cag gcc att cca ttc cag caa gtg gtg cca ctt ggc tct cct      1121
Glu Glu Gln Ala Ile Pro Phe Gln Gln Val Val Pro Leu Gly Ser Pro
            330                 335                 340 gtt tgt cga aaa aag agc gca atc taacaaattc tattccagca tgaacttcat     1175
Val Cys Arg Lys Lys Ser Ala Ile
    345                 350 tttaaaatgt aatggattat tatatttttt ataatgtagg attttaataa ttgattttta    1235
atgtgttatt ataaatattt ttataataag tatatttgta taaagtgtc  cagtccaacc    1295 a                                                                    1296

<210> SEQ ID NO 34
<211> LENGTH: 351
<212> TYPE: PRT
<213> ORGANISM: Drosophila melanogaster

<400> SEQUENCE: 34

Met Ala Pro Asn Asp Ala Val Ala Glu His Ala Glu Glu Gln Pro Lys
 1               5                  10                  15

Ile Ser Thr Phe Ala Val Leu Asp Leu Glu Thr Thr Asn Leu Pro Ala
                20                  25                  30

Tyr Arg Asn Asn Arg Val Ser Ile Thr Glu Leu Cys Ile Tyr Ala Phe
            35                  40                  45

Glu Ala Ala Leu Leu Lys Lys Lys Lys Glu Gln Asp Gln Asp Glu
        50                  55                  60

Gln Gln Glu Leu Pro Ala Ala Pro Arg Val Leu His Lys Leu Asn Val
65                  70                  75                  80

Leu Phe Gln Pro Ser Met Val Val Asp Pro Glu Ala Glu Arg Ile Thr
                85                  90                  95

Gly Leu Ser Asn Tyr Leu Leu Glu Arg Glu Ser Gln Leu Asp Thr Asp
            100                 105                 110

Ala Ala Gln Leu Ile Val Ser Phe Leu Lys His Leu Pro Ser Pro Val
        115                 120                 125

Cys Leu Val Ala His Asn Gly Trp Gly Phe Asp Phe Pro Ile Leu Arg
    130                 135                 140
```

-continued

```
Gln Ala Phe Glu Lys Leu Asn Ile Glu Leu Pro Gln Ser Leu Thr Cys
145                 150                 155                 160

Val Asp Ser Leu Arg Ala Phe Met Glu Ile Asp Asp Thr Gln Gln Lys
                165                 170                 175

Glu Thr Ser Gln Leu Lys Val Pro Asn Asp Val Gln Glu Ile Ile Pro
            180                 185                 190

Glu Leu Lys Pro Lys Gln Asn Thr Glu Thr Cys Leu Lys Glu Pro Glu
        195                 200                 205

Ala Val Val Asn Ile Asp Trp Arg Thr Arg Asn Glu Thr Thr Pro Asn
    210                 215                 220

Arg Pro Ile Leu Lys Pro Thr Glu Ala Phe Ala Lys Arg Lys Leu Leu
225                 230                 235                 240

Arg Asp Gly Asp Glu Asp Asp Leu Glu Glu Gln Thr Pro Pro Lys Arg
                245                 250                 255

Lys Pro Asp Glu Phe Arg Ser Arg Arg Gln Leu Phe Ser Gly Cys Lys
            260                 265                 270

Cys Ala Glu Asn Lys Arg Tyr Pro Pro Arg Gly Val Tyr Asn Leu Glu
        275                 280                 285

Ser Leu Tyr Thr Arg Ile Phe Lys Ile Pro Ala Leu Ser Ala His Gln
    290                 295                 300

Ala Glu Ala Asp Val Val Met Thr Thr Lys Leu Ile Gln His Tyr Gly
305                 310                 315                 320

Ile Asp Phe Leu Ala Phe Ala Glu Glu Gln Ala Ile Pro Phe Gln Gln
                325                 330                 335

Val Val Pro Leu Gly Ser Pro Val Cys Arg Lys Lys Ser Ala Ile
            340                 345                 350
```